United States Patent
Imamura et al.

(10) Patent No.: US 8,354,260 B2
(45) Date of Patent: Jan. 15, 2013

(54) PHANEROCHAETE CHRYSOSPORIUM CELLOBIOHYDROLASES AND COMPOSITIONS COMPRISING THE SAME

(75) Inventors: Chie Imamura, Nagoya (JP); Akinori Ikeuchi, Nagoya (JP); Haruo Takahashi, Ogaki (JP)

(73) Assignee: Kabushiki Kaisha Toyota Chuo Kenkyusho, Aichi-Gun (JP)

( * ) Notice: Subject to any disclaimer, the term of this patent is extended or adjusted under 35 U.S.C. 154(b) by 227 days.

(21) Appl. No.: 12/458,547

(22) Filed: Jul. 15, 2009

(65) Prior Publication Data

US 2010/0015662 A1 Jan. 21, 2010

(30) Foreign Application Priority Data

Jul. 15, 2008 (JP) ................................. 2008-184171
Jul. 15, 2009 (JP) ................................. 2009-166712

(51) Int. Cl.
*C12N 9/00* (2006.01)

(52) U.S. Cl. ....... 435/183; 435/209; 435/99; 435/254.2; 435/69.1

(58) Field of Classification Search .................. None
See application file for complete search history.

(56) References Cited

U.S. PATENT DOCUMENTS

2006/0205042 A1* 9/2006 Aehle et al. .................... 435/105

OTHER PUBLICATIONS

Henriksson et al. (Eur. J. Biochem., vol. 259, pp. 88-95, 1999).*
Cai et al. (Applied & Environmental Microbio, vol. 65, No. 2, Feb. 1999).*
Japanese Office Action mailed Jan. 25, 2011 issued in Japanese Patent Application No. 2009-166712.
Thomas M. Wood et al., "The Mechanism of Fungal Cellulase Action", Biochem. J., vol. 260, pp. 37-43, 1989.
Lu-Shan Wang et al., "Quantitative Estimate of the Effect of Cellulase Components During Degradation of Cotton Fibers", Carbohydrate Research, vol. 339, No. 4, pp. 819-824, 2004.
Martin Schülein, "Protein Engineering of Cellulases", Biochim. Biophys. Acta, vol. 1543, No. 2, pp. 239-252, 2000.
Uzcategui et al.; The 1,4-β-D-glucan cellobiohydrolases from *Phanerochaete chrysosporium*. I. A system of synergistically acting enzymes homologous to *Trichoderma reesei*; *Journal of Biotechnology*; 1991; pp. 271-285; No. 19.
Uzcategui et al.; The 1,4-β-D-glucan glucanohydrolases from *Phanerochaete chrysosporium*. Re-assessment of their significance in cellulose degradation mechanisms; *Journal of Biotechnology*; 1991; pp. 143-159; No. 21.
Henriksson et al.; Endoglucanase 28 (Cell2A), a new *Phanerochaete chrysosporium* cellulose; *European Journal of Biochemistry*; 1999; pp. 88-95; No. 259.
Tempelaars et al.; "Isolation, Characterization, and Analysis of the Expression of the *cbhII* Gene of *Phanerochaete chrysosporium*;" *Applied and Environmental Microbiology*; vol. 60; No. 12; Dec. 1994; pp. 4387-4393.
Dec. 27, 2011 Japanese Office Action issued in JP-2009-166712 (with English-language Translation).

* cited by examiner

*Primary Examiner* — Hope Robinson
(74) *Attorney, Agent, or Firm* — Oliff & Berridge, PLC

(57) ABSTRACT

A cellobiohydrolase that can contribute to a synergistic effect on cellulose degradation and the use of such cellobiohydrolase in cellulose degradation are provided. The synergistic effect is achieved by an enzyme preparation for cellulose degradation containing a cellobiohydrolase originating in *Phanerochaete chrysosporium* and belonging to GHF6 or a variant thereof, and an endoglucanase originating in a different source other than *Phanerochaete chrysosporium*.

18 Claims, 13 Drawing Sheets

SYNERGISTIC EFFECT ON CELLULOSE DEGRADATION OF
COMBINING OF AN ENDOGLUCANASE (EG)
AND CELLOBIOHYDROLASE (CBH)

SYNERGISTIC EFFECT ON CELLULOSE DEGRADATION OF COMBINING OF PcCBH2 AND AN ENDOGLUCANASE (EG) AND CELLOBIOHYDROLASE I(CBH I)

SYNERGISTIC EFFECT ON CELLULOSE DEGRADATION OF COMBINING OF
AoCBH2 AND AN ENDOGLUCANASE (EG) AND CELLOBIOHYDROLASE I(CBH I)

SYNERGISTIC EFFECT ON CELLULOSE DEGRADATION OF COMBINING OF
TrCBH2 AND AN ENDOGLUCANASE (EG) AND CELLOBIOHYDROLASE I(CBH I)

SYNERGISTIC EFFECT OF COMBINING WILD TYPE PcCBH2
AND VARIANT WITH BGL, EG AND CBHI (VARIANT: N=2)

DECOMPOSITION ACTIVITY IN PSC SOLUTION OF PcCBH2 (WILD TYPE)
AND VARIANT (AMOUNT OF REDUCING SUGARS)

DEGRADATION ACTIVITY IN AVICEL SOLUTION OF PcCBH2 (WILD TYPE) AND VARIANT (AMOUNT OF REDUCING SUGARS)

EFFECT OF ADDING VARIANT TO COMMERCIAL ENZYME PREPARATION (DEGRADATION ACTIVITY IN PSC SOLUTION)

ADDING EFFECT OF PcCBH2 (WILD TYPE)
TO COMMERCIAL PREPARATION

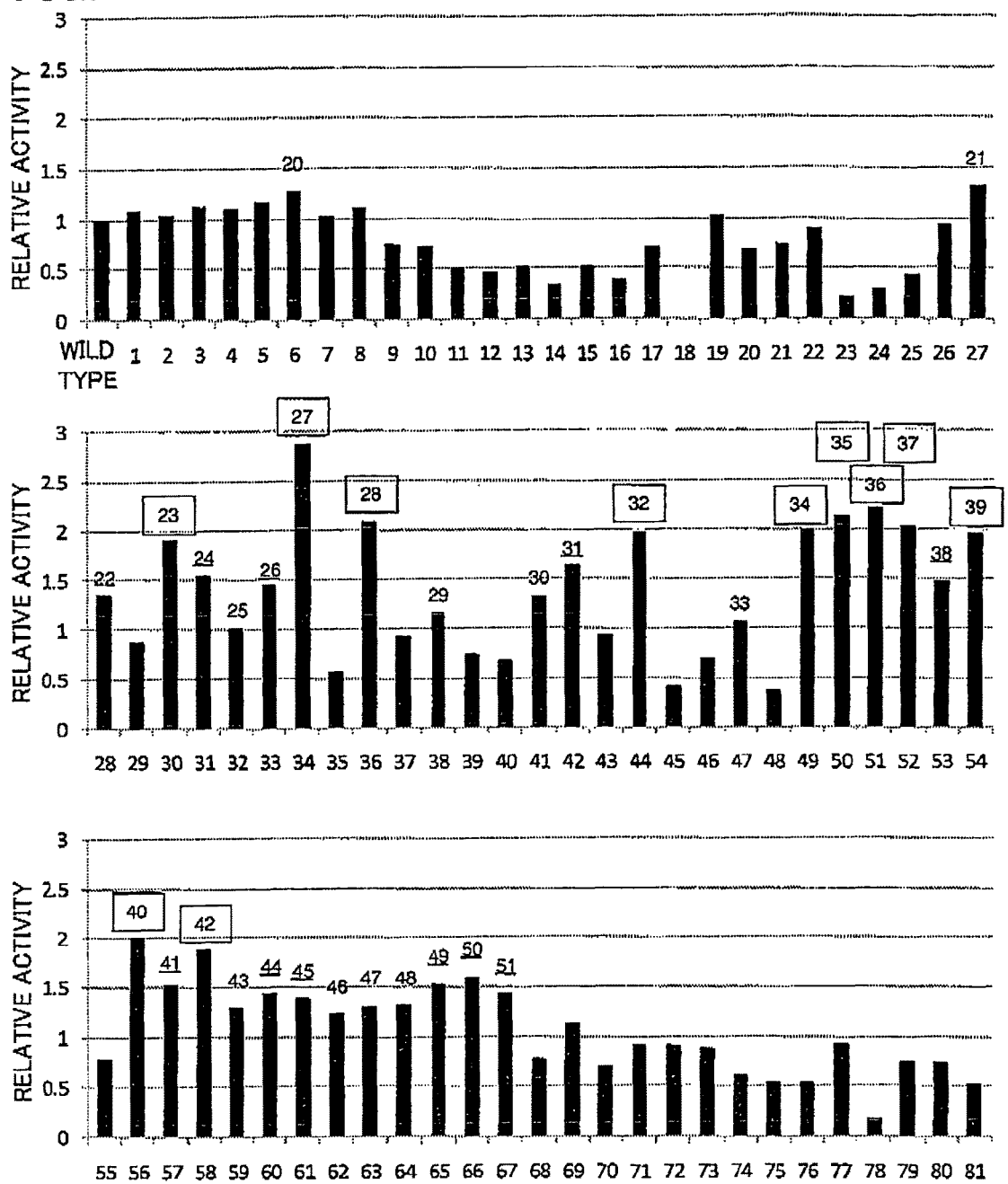

FIG. 13

NUMBERS IN BOXES ABOVE BARS REPRESENT VARIANTS WITH ACTIVITY 2 OR MORE TIMES GREATER THAN THE WILD TYPE (NUMBERS IN BOXES REPRESENT THE NUMBER OF A MUTATION OR VARIANT LISTED IN TABLE 2)

UNDERLINED NUMBERS ABOVE BARS REPRESENT VARIANTS WITH ACTIVITY 1.5 OR MORE TIMES GREATER THAN THE WILD TYPE (UNDERLINED NUMBERS REPRESENT THE NUMBER OF A MUTATION OR VARIANT LISTED IN TABLE 2)

PLAIN NUMBERS ABOVE BARS REPRESENT VARIANTS WITH ACTIVITY 1.3 OR MORE TIMES GREATER THAN THE WILD TYPE (NUMBERS REPRESENT THE NUMBER OF A MUTATION OR VARIANT LISTED IN TABLE 2)

PHANEROCHAETE CHRYSOSPORIUM CELLOBIOHYDROLASES AND COMPOSITIONS COMPRISING THE SAME

CROSS REFERENCE TO RELATED APPLICATION

The present application claims priority to Japanese Patent Application No. 2008-184171, filed on Jul. 15, 2008 and Japanese Patent Application No. 2009-166712, filed on Jul. 15, 2009, the contents of which are hereby incorporated into the present application by reference.

BACKGROUND OF THE INVENTION

1. Field of the Invention

The present invention relates to the use of cellobiohydrolase from *Phanerochaete* for the utilization of a biomass such as cellulose.

2. Description of the Related Art

In recent years, biomass created by the photosynthetic action of plants has shown increasing promise as an alternative to finite petroleum resources. Among these, the utilization of cellulose shows great promise. Cellulose is a polymer in which the sugar glucose is condensed via β-1,4 linkages, and it has a strong crystalline structure due to intermolecular hydrogen bonding. At least three types of cellulose degrading enzymes (cellulases) are required for the efficient degradation (saccharification) of cellulose to a monosaccharide, and it is thought that degradation only becomes possible through the cooperative action thereof (Hereinafter, this effect is referred to as a synergistic effect). These three types of cellulases are an exo-form (cleaving disaccharide units from the ends) cellobiohydrolase (CBH), and an endo-form (randomly cleaving) endoglucanase (EG) that both act directly on the cellulose polymer, and a β-glucosidase (BGL) that acts on oligomers of various sizes produced by these enzymes and breaks them down into monosaccharides.

Degradation of the polymer structure comprising crystalline cellulose presents great difficulties. There is a strong need for enzymes that can fully decompose such a structure, as well as for a combination thereof having a synergistic effect on cellulose degradation.

In light of this situation, combinations of different types of cellulases that can act most synergistically and decompose cellulose efficiently is being widely investigated. For example, it is known that one of the aforementioned three types of enzymes, cellobiohydrolase (CBH), comprises CBHI, a member of glycoside hydrolase family (GHF) 7 that cleaves from the reducing end of the cellulose chain, and CBHII, which is a member of GHF6 and cleaves from the non-reducing end. There have been various published reports concerning cellobiohydrolase. For example, it has been reported that among the forms of cellobiohydrolase produced by *Phanerochaete chrysosporium* (Pc), which belongs to the genus *Phanerochaete*, CBHI has a greater synergistic effect on cellulose degradation than CBHII when it is combined with a different type of cellulase. More specifically, a combination of CBHI produced by Pc and CBHI produced by an organism other than Pc was found to be superior to a combination of CBHI produced by Pc and CBHII produced by Pc (Uzcatsgui et al, J. Biotechnol. 19(2-3):271-85). Furthermore, a combination of CBHI produced by Pc (PcCBHI) and EG produced by Pc (PcEG) being superior to a combination of CBHII produced by Pc (PcCBHII) and EG produced by Pc (PcEG) has also been reported (Uzcatsgui et al, J. Biotechnol. 21(1-2):143-59).

It has also been reported that in the case of *Trichoderma reesei*, which belongs to the genus *Trichoderma*, the synergistic effect of CBHI on cellulose degradation is greater than that of CBHII when it is combined with a different type of cellulase. For example, it has been reported that a combination of PcEG III and TrCBHI is superior to a combination of PcEG III and TrCBHII (Henriksson et al, Eur. J. Biochem. 259 (1-2):88-95).

SUMMARY OF THE INVENTION

However, the above-referenced prior art and other references have not reported that the use of a combination of CBHII produced by *Phanerochaete chrysosporium* with a different type of cellulase is better than the use of a combination of CBHII and CBHI therefrom. In fact, there have been no specific reports of a synergistic effect between CBHII produced by *Phanerochaete chrysosporium* and an EG originating in a different microbial source.

Therefore, an object of the present invention is to provide a cellobiohydrolase that can contribute synergistically to cellulose degradation. A further object of the present invention is to provide the utilization of that cellobiohydrolase in the degradation of cellulose.

With the foregoing in view, the inventors focused on cellobiohydrolase among the enzymes necessary for cellulose degradation, and in particular, they focused on CBHII produced by *Phanerochaete chrysosporium* (PcCBHII). As noted above, PcCBHII has been judged inferior to PcCBHI with respect to its synergistic action on cellulose degradation, however when the inventors evaluated PcCBHII using a newly developed evaluation system, they discovered that PcCBHII is an enzyme that can contribute to the synergistic effect more than PcCBHI or a CBH originating in a different source. Furthermore, the inventors discovered that by modifying PcCBHII, it is possible to provide a CBHII that can contribute strongly to the synergistic effect. Based on these discoveries, the present teachings also provides means noted below.

Accordingly, in one aspect of the present teachings, an enzyme preparation for cellulose degradation, containing a cellobiohydrolase or variant thereof originating in *Phanerochaete chrysosporium* and belonging to GHF6; and an endoglucanase originating in a different source other than *Phanerochaete chrysosporium* is provided.

The variant may have an amino acid mutation in which serine is replaced by proline at position 22 or at a site corresponding thereto in the amino acid sequence represented by SEQ ID NO: 2. The variant may have one or more amino acid mutations selected from a group consisting of the mutations in the amino acid sequence represented by SEQ ID NO: 2 shown in the following Table 1 and mutations corresponding thereto.

TABLE 1

| TYPE OF MUTATION | | |
|---|---|---|
| GROUP I | 1 | S22P |
|  | 2 | Q2H |
|  | 3 | V21I |
|  | 4 | Y32H |
|  | 5 | S60L |
|  | 6 | L132V |
|  | 7 | T298S |
|  | 8 | F382S |
|  | 9 | S70F |
|  | 10 | V28A |

TABLE 1-continued

| | TYPE OF MUTATION | |
|---|---|---|
| | 11 | V21A |
| | 12 | S69P |
| | 13 | T157S |
| | 14 | N86D |
| | 15 | P275T |
| | 16 | L330F |
| | 17 | F382L |
| | 18 | N191H |
| | 19 | L29P |
| GROUP II | 20 | Y99T |
| | 21 | H263T |
| | 22 | H263F |
| | 23 | W266A |
| | 24 | W266E |
| | 25 | W266R |
| | 26 | W266S |
| | 27 | W266Y |
| | 28 | W266F |
| | 29 | W266N |
| | 30 | W266H |
| | 31 | W266D |
| | 32 | W266G |
| | 33 | W266L |
| | 34 | W269A |
| | 35 | W269E |
| | 36 | W269R |
| | 37 | W269S |
| | 38 | W269Y |
| | 39 | W269T |
| | 40 | W269M |
| | 41 | W269N |
| | 42 | W269Q |
| | 43 | W269K |
| | 44 | W269H |
| | 45 | W269D |
| | 46 | W269C |
| | 47 | W269G |
| | 48 | W269P |
| | 49 | W269I |
| | 50 | W269L |
| | 51 | W269V |

The endoglucanase originating in a different source is preferably one or more type selected from endoglucanases belonging to GHF5, GHF7, GHF12, and GHF45. The endoglucanases originating in different sources and belonging to GHF5 can comprise one or more selected from endoglucanases originating in *Trichoderma reesei, Aspergillus niger* and *Aspergillus oryzae*, the endoglucanase originating in different sources and belonging to GHF12 can comprise one or more selected from endoglucanases originating in *Trichoderma reesei* and an endoglucanase originating in *Aspergillus niger*, and the endoglucanase originating in different sources and belonging to GHF7 can comprise one or more selected from endoglucanases originating in *Trichoderma reesei* and *Aspergillus oryza*. Further, the endoglucanase originating in a different source and belonging to GHF45 can comprise one or more endoglucanases selected from endoglucanases originating in *Trichoderma reesei* and *Aspergillus oryza*.

Further, the enzyme preparation can comprise one or more cellobiohydrolases belonging to GHF7. The enzyme preparation may comprise a cellulase composition originating in *Trichoderma reesei* or a transformant thereof. The enzyme preparation may contains essentially no β-glucosidase.

Another aspect of the present teaching, a cellulose decomposition activity enhancer comprising a cellobiohydrolase originating in *Phanerochaete chrysosporium* and belonging to GHF6, and used in combination with a different cellulase for cellulose decomposition is provided. In the enhancer, the different cellulase comprises one or more types selected from endoglucanases originating in different sources other than *Phanerochaete chrysosporium*. The endoglucanases originating in different sources may comprise one or more types selected from endoglucanases belonging to GHF5, GHF7, GHF12, and GHF45. Preferably, the endoglucanases originating in different sources can comprise one or more selected from endoglucanases belonging to *Trichoderma reesi, Aspergillus niger*, and *Aspergillus oryzae* as its source.

In another aspect of the present teachings, a protein having an amino acid mutation in which serine is replaced by proline at position 22 in the amino acid sequence represented by SEQ ID NO: 2 or a position corresponding thereto, and having the activity of a cellobiohydrolase belonging to GHF6 is provided. The protein may have the amino acid sequence represented by SEQ ID NO: 4.

In a further aspect of the present teachings, a protein having one or more amino acid mutations selected from a group consisting of the mutations in the amino acid sequence represented by SEQ ID NO: 2 shown in Table 1 and mutations corresponding thereto, and having the activity of a cellobiohydrolase belonging to GHF6 is provided.

In a still further aspect of the present teachings, a protein having the amino acid mutations in the amino acid sequence represented by SEQ ID NO: 2 shown in Table 2 or mutations corresponding thereto, and having the activity of a cellobiohydrolase belonging to GHF6 is provided.

TABLE 2

| TYPE OF VARIANT | TYPES OF MUTATIONS INCLUDED IN VARIANTS | | | |
|---|---|---|---|---|
| 1 | Q2H | | | |
| 2 | S22P | V21I | Y32H | |
| 3 | S22P | Y32H | | |
| 4 | S22P | S60L | | |
| 5 | S22P | L132V | T298S | P382S |
| 6 | S22P | S70F | L132V | F382S |
| 7 | S22P | V28A | | |
| 8 | S22P | V21A | S69P | |
| 9 | S22P | V21A | S69P | T157S |
| 10 | S22P | N86D | P275T | L330F | F382L |
| 11 | S22P | Q2H | N191H | |
| 12 | S22P | Q2H | L29P | N191H |
| 13 | S22P | V21A | | |
| 14 | S22P | L29P | | |
| 15 | S22P | S69P | | |
| 16 | S22P | S70F | | |
| 17 | S22P | L132V | | |
| 18 | S22P | N191H | | |
| 19 | S22P | F382S | | |
| 20 | Y99T | | | |
| 21 | H263T | | | |
| 22 | H263F | | | |
| 23 | W266A | | | |
| 24 | W266E | | | |
| 25 | W266R | | | |
| 26 | W266S | | | |
| 27 | W266Y | | | |
| 28 | W266F | | | |
| 29 | W266N | | | |
| 30 | W266H | | | |
| 31 | W266D | | | |
| 32 | W266G | | | |
| 33 | W266L | | | |
| 34 | W269A | | | |
| 35 | W269E | | | |
| 36 | W269R | | | |
| 37 | W269S | | | |
| 38 | W269Y | | | |
| 39 | W269T | | | |
| 40 | W269M | | | |
| 41 | W269N | | | |
| 42 | W269Q | | | |
| 43 | W269K | | | |
| 44 | W269H | | | |

TABLE 2-continued

| TYPE OF VARIANT | TYPES OF MUTATIONS INCLUDED IN VARIANTS | | | | | |
|---|---|---|---|---|---|---|
| 45 | W269D | | | | | |
| 46 | W269C | | | | | |
| 47 | W269G | | | | | |
| 48 | W269P | | | | | |
| 49 | W269I | | | | | |
| 50 | W269L | | | | | |
| 51 | W269V | | | | | |
| 52 | Q2H | S22P | L29P | N191H | V28A | |
| 53 | Q2H | S22P | L29P | N191H | S60L | |
| 54 | Q2H | S22P | L29P | N191H | W269M | |
| 55 | Q2H | S22P | L29P | N191H | W269M | V28A |
| 56 | Q2H | S22P | L29P | N191H | W269M | S60L |
| 57 | Q2H | S22P | L29P | N191H | W269A | |
| 58 | Q2H | S22P | L29P | N191H | W269R | |

In a further aspect of the present teachings, a DNA construct comprising DNA encoding the protein according to any of the protein of the present teachings is provided. This DNA construct may be an expression vector. In a still further aspect of the present teaching, a transformant transformed by the DNA construct is provided.

In a still further aspect of the present teachings, a transformant originating in *Phanerochaete chrysosporium* and expressing a cellobiohydrolase belonging to GHF6 or variant thereof, and an endoglucanase originating in a different source other than *Phanerochaete chrysosporium* is provided. This transformant may have the cellobiohydrolase or variant thereof and the endoglucanase originating in a different source which are retained on the surface of the cell or are secreted extracellularly. The expression of β-glucosidase is inhibited in the transformant. The expression of endogenous cellulases which are cellulases other than the cellobiohydrolase or variant thereof and the endoglucanase originating in a different source, is inhibited in the transformant. The transformant may be a non-cellulase producing organism.

In an additional aspect of the present teachings, a process for producing an enzyme preparation for cellulose degradation is provided. In this method, a cellobiohydrolase originating in *Phanerochaete chrysosporium* and belonging to GHF6 or a variant thereof, and an endoglucanase originating in a different source other than *Phanerochaete chrysosporium* are produced using the transformant.

In another aspect of the present teachings, a process for producing a low molecular weight cellulose product, is provided. This method may comprise a step of converting cellulose to a low molecular weight product, using a cellobiohydrolase originating in *Phanerochaete chrysosporium* and belonging to GHF6 or a variant thereof, and an endoglucanase originating in different sources other that *Phanerochaete chrysosporium* in the presence of cellulose. In this method, the step of conversion to a low molecular weight product is a step in which cellulose is decomposed without the presence of β-glucosidase to obtain cellulose oligomers. In the step of conversion to a low molecular weight product, lignin and/or hemicellulose may exist together with cellulose.

In yet another aspect of the present teachings, a process for producing a useful substance having cellulose as a raw material is provided. The process comprises the steps of degrading cellulose using a cellobiohydrolase originating in *Phanerochaete chrysosporium* and belonging to GHF6 or a variant thereof, and an endoglucanase originating in a different source other than *Phanerochaete chrysosporium* in the presence of cellulose and without the presence of β-glucosidase and obtaining oligomers; and degrading the cellulose oligomers with β-glucosidase and obtaining glucose. In this process, the glucose production step may be an ethanol fermentation step in which the cellulose oligomers are decomposed using a ethanol producing microorganizm expressing β-glucosidase and the resulting glucose is used as a carbon source. Further, in the process, the glucose production step is an organic acid fermentation step in which the cellulose oligomers are decomposed using an organic acid-producing microorganism expressing β-glucosidase and the resulting glucose is used as a carbon source.

BRIEF DESCRIPTION OF THE DRAWINGS

FIG. 13 is a graph showing the evaluation of the synergistic effect of site specific mutations in the vicinity of the substrate binding tunnel;

DESCRIPTION OF THE PREFERRED EMBODIMENTS

Figure 1:
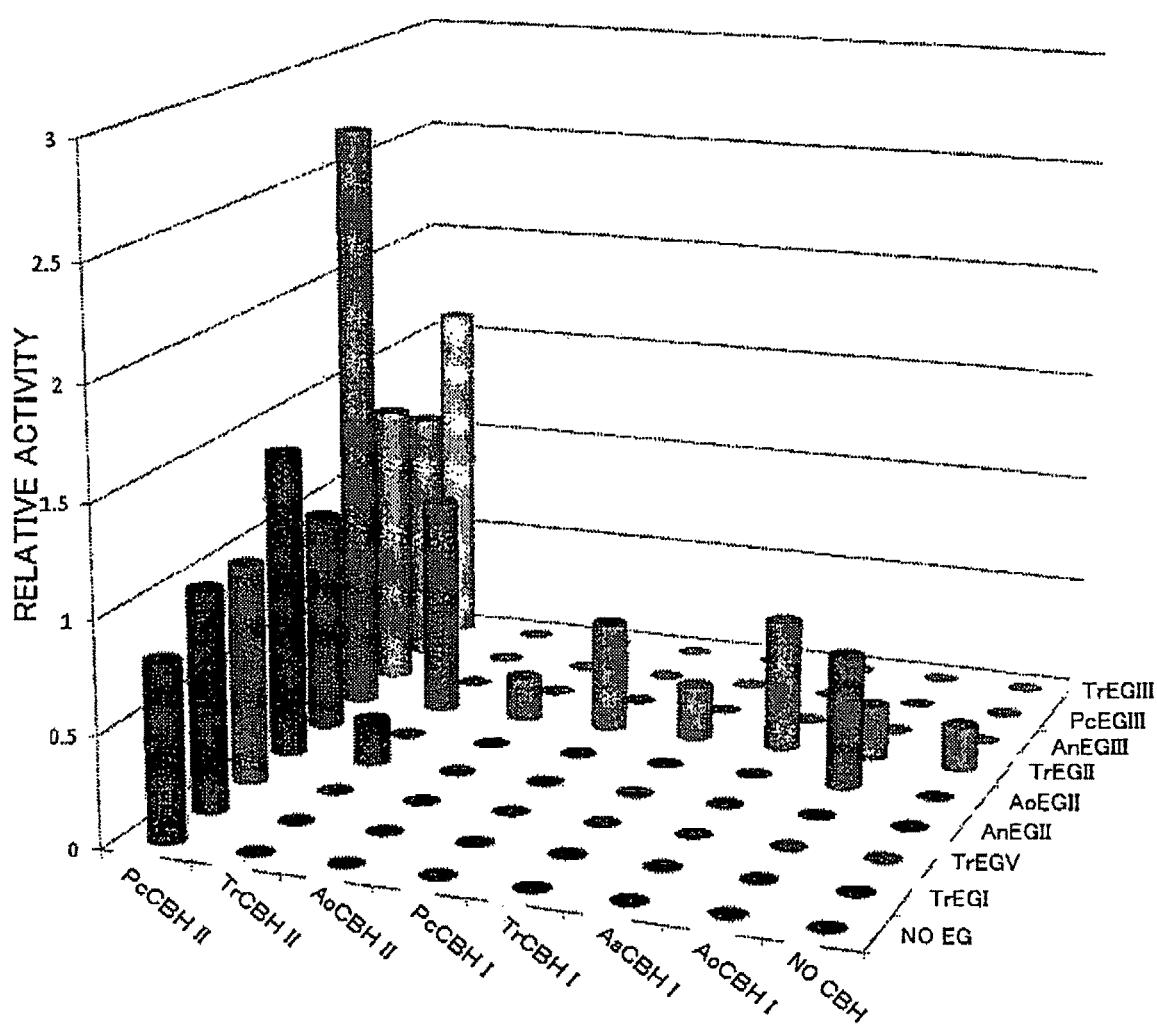
FIG. 1 is a graph showing the evaluation of the synergistic effect on cellulose degradation of various combinations of cellobiohydrolase and endoglucanase.

The present teachings relates to the combination of cellobiohydrolase originating in *Phanerochaete chrysosporium* and belonging to GHF6 or a variant thereof and an endoglucanase originating in a different source. The present teachings also relates to an enzyme preparation for cellulose degradation and a cellulose degradation activity enhancer containing the same, a transformant expressing cellulases in such a combination, a process for producing this enzyme preparation, a process for producing a useful material utilizing such a combination, and the like.

In accordance with the present teachings, the cellobiohydrolase originating in *Phanerochaete chrysosporium* and belonging to GHF6 or the variant thereof can contribute excellently to a synergistic effect on the degradation of cellulose through being combined with an endoglucanase originating in a variety of different sources. As a result, cellulose can be decomposed efficiently by these combinations of cellobiohydrolase and an endoglucanase originating in a different source. Thus, by using the combination in a process step upstream of various steps that utilize glucose, cellulose oligomers and glucose can thereby be efficiently produced, and these can then be utilized as the carbon source for fermentation. Further, by using the combination cellulose can be degraded efficiently under existing lignin and/or hemicellulose originating biomass such as lignocellulose based material.

The preferred embodiments of the present teachings are described below. First the cellobiohydrolase originating in *Phanerochaete chrysosporium* and belonging to GHF6, and a variant thereof will be described, and this will be followed by descriptions of processes for producing and utilizing the same as an enzyme preparation and a cellulose degradation activity enhancer. A classification of cellulases according to GHF (Glycoside Hydrolase Family) is provided on the CAZy (Carbohydrate Active Enzymes) home page (www.cazy.org/fam/acc_GH.html).

(Cellobiohydrolase Originating in *Phanerochaete chrysosporium* and Belonging to GHF6)

The expression "originating in *Phanerochaete chrysosporium*" used herein refers a cellobiohydrolase (CBHII) belonging to GHF6 that is produced by a microorganism (either a wild strain or variant strain) included in the category of *Phanerochaete chrysosporium* or a CBHII obtained by genetic engineering methods utilizing a gene encoding a protein produced by that microorganism. Therefore, a CBHII that is a recombinant protein produced by a transformant transfected with a gene encoding CBHII obtained from *Phanerochaete chrysosporium* (or a modified gene thereof) also corresponds to a CBHII originating in *Phanerochaete chrysosporium*.

(PcCBH2)

One aspect of CBHII in the present teachings is CBHII isolated from naturally occurring *Phanerochaete chrysosporium* (hereinafter, called PcCBH2 to distinguish it from variants thereof). A typical amino acid sequence thereof is listed as SEQ ID NO: 2 (Appl. Environ. Microbiol. 60(12), 4387-4393 (1994)).

The PcCBH2 of the present teachings can be collected from individual strains of this species provided it is a CBHII originating in *Phanerochaete chrysosporium*. For example, it can be collected from a different strain of *Phanerochaete chrysosporium* based on the amino acid sequence represented by SEQ ID NO: 2. The PcCBH2 can have an amino acid sequence that is at least 75% homologous with the amino acid sequence represented by SEQ ID NO: 2, and it can comprise an amino acid sequence of the aforesaid level of homology.

The PcCBH2 preferably is 80% or more homologous, more preferably 85% or more homologous, even more preferably 90% or more homologous, and most preferably 95% or more homologous with the amino acid sequence represented by SEQ ID NO: 2. The level of homology with a specific amino acid sequence can be obtained utilizing a program such as protein blast or blastx that uses a blastp, psi-blast, or phi-blast algorithm and can be run on the NCBI home page (www.ncbi.nlm.nih.gov/).

The PcCBH2 may, alternatively, be an amino acid sequence encoded by DNA that hybridizes under stringent conditions with, as the probe, all or some portion of a polynucleotide (e.g., the base sequence set forth in SEQ ID NO:1) coding for the amino acid sequence set forth in SEQ ID NO:2. "Hybridizes under stringent conditions" herein refers to a DNA base sequence which is obtained by, for instance, colony hybridization, plaque hybridization or Southern hybridization using DNA as the probe. This is exemplified by DNA which, after carrying out hybridization at 65° C. and in the presence of 0.7 to 1.0 M NaCl using a filter on which DNA from a colony or plaque, or fragments of such DNA, has been immobilized, can be identified by washing the filter at 65° C. using a 0.1× to 2×SSC solution (a 1×SSC solution contains 150 mM sodium chloride and 15 mM sodium citrate) at 65° C. Hybridization may be carried out according to a method described in, for example, *Molecular Cloning: A Laboratory Manual*, $3^{rd}$ Ed., (Cold Spring Harbor Laboratory Press; Cold Spring Harbor, N.Y.; 1989) (referred to below as "*Molecular Cloning*, $3^{rd}$ Ed.") or *Current Protocols in Molecular Biology*, Supplements 1 to 38 (John Wiley & Sons, 1987-1997) (referred to below as "*Current Protocols in Molecular Biology*"). DNA hybridized under stringent conditions is exemplified by DNA having at least a given homology to the base sequence of the DNA used as the probe. Examples include DNA having a homology of at least 70%, preferably at least 80%, more preferably at least 90%, even more preferably at least 93%, yet more preferably at least 95%, and most preferably at least 98%.

The PcCBH2 may include an amino acid sequence having, in the amino acid sequence set forth in SEQ ID NO:2 or a homologous amino acid sequence, one or more amino acid mutations, or may consist of such an amino acid sequence. The number of amino acid mutations is not subject to any particular limitation and may be, for example, from 1 to about 40, preferably from 1 to about 30, more preferably from 1 to about 20, even more preferably from 1 to about 10, still more preferably from 1 to about 5, and most preferably from 1 to about 3. The amino acid mutations may be in the form of amino acid substitutions, deletions or additions, or any combination of two or more of these types of modifications.

(PcCBH2 Variant)

A PcCBH2 variant is a protein having CBHII activity wherein an amino acid mutation has been artificially introduced into the amino acid sequence represented by SEQ ID NO: 2. The expression "having CBHII activity" means that it is sufficient to have a CBHII activity, preferably it has a synergistic effect on cellulose degradation equal to or greater than that of PcCBH2.

The amino acid mutation may be introduced by various techniques. For example, use may be made of the method of modifying the genetic information such as DNA encoding the amino acid sequence set forth in SEQ ID NO:2 or a homologous sequence. Known techniques such as the Kunkel method or the gapped duplex method, or methods in general accordance therewith, may be employed to introduce the changes in the DNA, modify the genetic information and obtain the inventive protein. For example, modifications may be introduced into the DNA by using a mutagenesis kit that employs site-specific mutagenesis (e.g., MUTAN-K and MUTAN-G, both available from Takara). Alternatively, gene mutagenesis or the construction of a chimeric gene may be carried out by a technique such as error-prone PCR or DNA shuffling. Error-prone PCR and DNA shuffling are known techniques in the field of the present teachings. For example, reference may be made to Chen, K. and Arnold, F. H.: *Proc. Natl. Acad. Sci. U.S.A.* 90:5618-5622 (1993) concerning error-prone PCR. With regard to molecular evolution engineering technique such as DNA shuffling and cassette PCR, reference may be made to, for example, Kurtzman, A. L., Govindarajan, S., Vahle, K., Jones, J. T., Heinrichs, V., Patten, P. A.: "Advances in directed protein evolution by recursive genetic recombination: Applications to therapeutic proteins," *Curr. Opinion Biotechnol.* 12, 361-370 (2001), and Okuta, A., Ohnishi, A. and Harayama, S.: PCR isolation of catechol 2,3-dioxygenase gene fragments from environmental samples and their assembly into functional genes," *Gene* 212, 221-228 (1998). Of these, it is preferable to employ a non-cellular protein synthesis system which utilizes a molecular evolution technique involving the introduction of random mutations such as by error-prone PCR. The non-cellular protein synthesis system applied for error-prone PCR may be a protein synthesis system which is publicly known or has been disclosed in Japanese Patent Application Publication Nos. 2006-61080 and 2003-116590 filed by the present patent applicant. Active enzymes can easily be obtained by using these non-cellular protein synthesis systems described by the patent applicant. Hence, error-prone PCR in which such a protein synthesis system has been applied may be advantageously used as the technique for acquiring the protein of the present teachings.

An example of a variant has a sequence in which serine is replaced by proline at position 22 in the amino acid sequence of SEQ ID NO: 2 (S22P) or a position corresponding thereto. This amino acid sequence is shown in SEQ ID NO: 4, and one example of a DNA base sequence encoding that amino acid sequence is shown in SEQ ID NO: 3. A position corresponding to position 22 of the amino acid sequence represented by SEQ ID NO: 2 can be determined by carrying out alignment on a protein (variant) while considering the homology of the amino acid sequence thereof with respect to the amino acid sequence represented by SEQ ID NO: 2. In other words, it is possible to determine the position of the serine that corresponds to position 22 of SEQ ID NO: 2 in that other protein by alignment as the "position corresponding to position 22 of the amino acid sequence represented by SEQ ID NO: 2."

Additionally, variants may include proteins having an amino acid sequence having one or more of the amino acid mutations selected from a group consisting of the mutations shown in the following table 3 in the amino acid sequence represented by SEQ ID NO: 2 and mutations corresponding thereto. In this case, "mutations corresponding thereto" can be determined by carrying out alignment on a different protein (variant) while considering the homology of the amino acid sequence thereof with respect to the amino acid sequence represented by SEQ ID NO: 2. In other words, it is possible to determine the position in that other protein that corresponds to the site of a specific amino acid mutation in SEQ ID NO: 2 by alignment as an "amino acid mutation corresponding to an amino acid mutation in the amino acid sequence represented by SEQ ID NO: 2." Therefore, a variant does not have both of a certain amino acid mutation and the mutation corresponding thereto at the variant.

In the following table 3, the amino acid mutations belonging to Group I are mutations related to the entire region of the cellobiohydrolase consisting of the amino acid sequence represented by SEQ ID NO: 2, and the amino acid mutations belonging to Group II are mutations in the vicinity of the substrate binding tunnel of that cellobiohydrolase. Preferably, an amino acid mutation belonging to Group I in the following table is used in combination with an amino acid mutation belonging to Group II. Furthermore, in the following table, the use of a mutation whose effectiveness is labeled as "*" is preferred, the use of a mutation whose effectiveness is labeled as "" is more preferred, and the use of a mutation whose effectiveness is labeled as "*" is even more preferred.

TABLE 3

| TYPE OF MUTATION | | | EFFECTIVITY |
|---|---|---|---|
| GROUP I | 1 | S22P | *** |
| | 2 | Q2H | *** |
| | 3 | V21I | |
| | 4 | Y32H | |
| | 5 | S60L | *** |
| | 6 | L132V | |
| | 7 | T298S | |
| | 8 | F382S | |
| | 9 | S70F | |
| | 10 | V28A | *** |
| | 11 | V21A | |
| | 12 | S69P | |
| | 13 | T157S | |
| | 14 | N86D | |
| | 15 | P275T | |
| | 16 | L330F | |
| | 17 | F382L | |
| | 18 | N191H | *** |
| | 19 | L29P | *** |
| GROUP II | 20 | Y99T | * |
| | 21 | H263T | * |
| | 22 | H263F | * |
| | 23 | W266A | *** |
| | 24 | W266E | ** |
| | 25 | W266R | * |
| | 26 | W266S | ** |
| | 27 | W266Y | *** |
| | 28 | W266F | *** |
| | 29 | W266N | * |
| | 30 | W266H | * |
| | 31 | W266D | ** |
| | 32 | W266G | *** |
| | 33 | W266L | * |
| | 34 | W269A | *** |
| | 35 | W269E | *** |
| | 36 | W269R | *** |
| | 37 | W269S | *** |
| | 38 | W269Y | ** |
| | 39 | W269T | *** |
| | 40 | W269M | *** |
| | 41 | W269N | *** |
| | 42 | W269Q | *** |
| | 43 | W269K | * |
| | 44 | W269H | ** |
| | 45 | W269D | ** |
| | 46 | W269C | * |
| | 47 | W269G | * |
| | 48 | W269P | * |
| | 49 | W269I | ** |
| | 50 | W269L | ** |
| | 51 | W269V | ** |

More specifically, variants may include proteins having amino acid mutations shown in "varieties of mutations included in variant" in Table 4 in the amino acid sequence represented by SEQ ID NO: 2. Each variant can include one or more substitutions of mutations with the mutations corresponding thereto. Among these, in the following table the use of a mutation whose effectiveness is labeled as "" is preferred, and the use of a mutation whose effectiveness is labeled as "*" is more preferred. In particular, when one of the variants listed as variants 52 to 58 was combined with BGL, EG, and CBHI, the cellulose degradation activity was at least 4.5 times (and the maximum was roughly 6.5 times) that of the parent strain (wild type).

TABLE 4

| TYPE OF VARIANT | TYPES OF MUTATIONS INCLUDED IN VARIANTS | | | | | EFFECTIVITY |
|---|---|---|---|---|---|---|
| 1 | Q2H | | | | | *** |
| 2 | S22P | V21I | Y32H | | | *** |
| 3 | S22P | Y32H | | | | *** |
| 4 | S22P | S60L | | | | *** |
| 5 | S22P | L132V | T298S | F382S | | *** |
| 6 | S22P | S70F | L132V | F382S | | *** |
| 7 | S22P | V28A | | | | *** |
| 8 | S22P | V21A | S69P | | | *** |
| 9 | S22P | V21A | S69P | T157S | | *** |
| 10 | S22P | N86D | P275T | L330F | F382L | *** |
| 11 | S22P | Q2H | N191H | | | *** |
| 12 | S22P | Q2H | L29P | N191H | | *** |
| 13 | S22P | V21A | | | | ** |
| 14 | S22P | L29P | | | | *** |
| 15 | S22P | S69P | | | | ** |
| 16 | S22P | S70F | | | | ** |
| 17 | S22P | L132V | | | | ** |
| 18 | S22P | N191H | | | | *** |
| 19 | S22P | F382S | | | | ** |
| 20 | Y99T | | | | | * |
| 21 | H263T | | | | | * |
| 22 | H263F | | | | | * |
| 23 | W266A | | | | | *** |
| 24 | W266E | | | | | ** |
| 25 | W266R | | | | | * |
| 26 | W266S | | | | | ** |
| 27 | W266Y | | | | | *** |
| 28 | W266F | | | | | *** |
| 29 | W266N | | | | | * |
| 30 | W266H | | | | | * |
| 31 | W266D | | | | | ** |
| 32 | W266G | | | | | *** |
| 33 | W266L | | | | | * |
| 34 | W269A | | | | | *** |
| 35 | W269E | | | | | *** |
| 36 | W269R | | | | | *** |
| 37 | W269S | | | | | *** |
| 38 | W269Y | | | | | ** |
| 39 | W269T | | | | | *** |
| 40 | W269M | | | | | *** |
| 41 | W269N | | | | | ** |
| 42 | W269Q | | | | | *** |
| 43 | W269K | | | | | * |
| 44 | W269H | | | | | ** |
| 45 | W269D | | | | | ** |
| 46 | W269C | | | | | * |
| 47 | W269G | | | | | * |
| 48 | W269P | | | | | * |
| 49 | W269I | | | | | ** |
| 50 | W269L | | | | | ** |
| 51 | W269V | | | | | ** |
| 52 | Q2H | S22P | L29P | N191H | V28A | *** |
| 53 | Q2H | S22P | L29P | N191H | S60L | *** |
| 54 | Q2H | S22P | L29P | N191H | W269M | *** |
| 55 | Q2H | S22P | L29P | N191H | W269M V28A | *** |
| 56 | Q2H | S22P | L29P | N191H | W269M S60L | *** |
| 57 | Q2H | S22P | L29P | N191H | W269A | *** |
| 58 | Q2H | S22P | L29P | N191H | W269R | *** |

When the PcCBH2 or variant thereof in the present teachings is combined with an endoglucanase originating in a different source, it has a synergistic effect on cellulose degradation. This synergistic effect can be evaluated by the evaluation system created by the inventors that will be described below (e.g., the evaluation system disclosed in Japanese Patent Application 2007-243626). The contents of the specification are hereby incorporated into the present application by reference.

For the synergistic effect on cellulose, PcCBH2 or a variant thereof is supplied to evaluation areas consisting of a solid phase support containing cellulose, the cellulose in those areas of the solid phase support is decomposed. The areas where cellulose is decomposed make a halo pose which have relative size with respect to amount of the decomposed cellulose. Different celluloses and the like (i.e., cellulases comprising the various combinations herein) can be supplied in combinations to the above evaluation areas to assay the synergic effect of cellulases.

A halo based on cellulose disappearance in the solid-phase body generally forms as an area that is more transparent than its surroundings, and can be directly confirmed visually or in some other manner. At the time of halo detection, the halo can be clearly detected by dyeing the cellulose with a dye such as Congo Red. Alternatively, when a dye-linked cellulose (e.g., CELLULOSE AZURE, available from Sigma) is used as the biomass, the dye diffuses into the solid-phase body with degradation of the cellulose, enabling the cellulose degrading activity to be readily detected. Similarly, by employing a fluorescent dye-linked cellulose as the biomass, a halo can easily be detected. Also, in cases where acid-treated cellulose or the like is used as the biomass, a distinct halo forms due to cellulose degradation, enabling the cellulose degradation activity to be easily detected. Carboxymethyl cellulose (CMC) may be used to detect the halo. Alternatively, the reducing sugar which forms as a result of cellulose degradation may be detected by the DNS method or the Somogyi-Nelson method using CMC or the like as the substrate.

The solid-phase body for halo formation is exemplified by a biomass-supporting gel or film. The material making up the gel or film is not subject to any particular limitation; advantageous use may be made of a natural or artificial polymeric material. Preferred use may be made of agarose (agar) as such a polymeric material. The solid-phase body may be obtained by, for example, suspending or dissolving cellulose that has been purified to some degree as the biomass in an agarose solution, followed by solidification under specific conditions. Alternatively, a powder obtained by drying and pulverizing unpurified biomass may be suspended in an agarose solution, then solidified to give the solid-phase body. No particular limitation is imposed on the morphology of the solid-phase body and the amount of cellulose contained in the solid-phase body, other than the morphology and the amount of cellulose be such as to enable detection of the endoglucanase activity. To detect a halo, carboxymethylcellulose (CMC), phosphate swallen cellulose (PSC), Avicel can be used. To estimate the synergic effect of cellulases against insoluble cellulose having crystalline structure, PSC and Avicel are used preferably.

The evaluation of the synergistic effect is not limited to a method using a solid phase support. For example, predetermined amounts of BGL, EG, and CBHI are added to a cellulose-containing aqueous solution such as 1% PSC, into which a variant of the present teachings and the like is added, whereas the cellulose is decomposed using a suitable temperature and time, and then the amount of reducing sugars produced thereby can be measured by a tetrazolium blue chloride (TZ) assay or Nelson-Somogyi assay.

Apart from being obtained by a genetic engineering technique with a non-cellular protein synthesis system such as that described above, the inventive protein may be obtained by a genetic engineering technique that involves transforming a suitable host cell with DNA coding for the inventive protein and inducing the transformant to produce the protein of the present teachings. The production of genetically engineered protein using a transformant may be carried out in general accordance with a method described in, for example, *Molecular Cloning, 3rd* or *Current Protocols in Molecular Biology*.

In cases where the inventive protein is a protein produced by the genus *Phanerochaete*, this protein may be obtained by culturing a genus *Phanerochaete* organism such as *Phanerochaete chrysosporium* on a medium, collecting the culture supernatant, isolating the PcCBH2 or variant thereof in the present teachings from the culture supernatant, and purification. Isolation and purification may be carried out using known protein isolation and purification techniques. Nor is it always necessary to isolate and purify the PcCBH2 or variant thereof in the present teachings from the culture supernatant. It is also possible to use the culture supernatant directly as the genus *Phanerochaete* endoglucanase. Nor is it always necessary to isolate and purify the PcCBH2 or variant thereof from the culture supernatant. It is also possible to use the culture supernatant directly as the PcCBH2 or variant thereof.

(Enzyme Preparation for Cellulose Degradation)

The enzyme preparation for cellulose degradation of the present teachings can contain PcCBH2 and/or a variant thereof (hereinafter, the term "PcCBH2, etc." is simply used in place of "PcCBH2 and/or a variant thereof" provided there is no particular need to distinguish between PcCBH2 and a variant thereof) and an endoglucanase originating in a different source other than *Phanerochaete chrysosporium*. The present inventors originally discovered that PcCBH2, etc., imparts a strong synergistic effect for cellulose degradation when cellulose is decomposed by combining the same with the endoglucanase originating in the source other than *Phanerochaete chrysosporium*. Therefore, an enzyme preparation in which PcCBH2, etc., and an endoglucanase originating in a different source are combined is useful for cellulose degradation.

The cellulose in the present specification is polymers obtained by the polymerization of glucose with β-1,4-glucosidic linkages, and derivatives thereof. The degree of glucose polymerization is not subject to any particular limitation. Derivatives include those obtained by carboxymethylation, aldehyde conversion, or esterification. Alternatively, "cellulose" may refer to a partial degradation product of cellulose, such as cello-oligosaccharide or cellobiose. Or "cellulose" may refer to β-glucoside (a glycoside), lignocellulose, which is a complex of cellulose with lignin and/or hemicellulose, or may refer to a complex of cellulose with pectin. The cellulose may be crystalline cellulose or amorphous cellulose. Moreover, the cellulose may be of natural origin or may be one that has been artificially synthesized. Nor is there any particular limitation on the source of the cellulose. That is, the cellulose may be of plant origin, fungal origin, or bacterial origin. Moreover, "cellulose" may refer to a cellulose-containing material which contains any of the foregoing celluloses. Exemplary cellulose-containing materials include natural fiber products such as cotton and linen, reconstituted fiber products such as rayon, cuprammonium rayon, acetate and lyocell; and biomass such as Lignocellulose-based agricultural waste products including rice straw, rice hulls, wood chips and or so. Pre-treated biomass can also be used. Lignocellulose-based agricultural waste such as wood chips can be raised as an example.

For the endoglucanase originating in a different source, the "different source" means a microorganism other than *Phanerochaete chrysosporium*, and is not particularly limited thereto provided it is one other than *Phanerochaete chrysosporium*. Examples include publicly known cellulase-producing fungi such as *Trichoderma reesei, Aspergillus aculeatus, Aspergillus niger, Aspergillus oryzae, Clostridium thermocellum, Hemicola insolens*, and *Chaetomium globosum*. Among the above, *Trichoderma reesei, Aspergillus aculeatus*, and *Aspergillus niger* are preferred, and *Trichoderma reesei* is even more preferred.

Various types of publicly known endoglucanases can be noted as the examples of an endoglucanase originating in a different source, and such an endoglucanase can either be used alone or in a suitable combination of two or more types thereof. For example, an endoglucanase belonging to GHF5 can be noted. From among the endoglucanases belonging to GHF5, the use of an endoglucanase originating in *Trichoderma reesei*, an endoglucanase originating in *Aspergillus oryzae*, and an endoglucanase originating in *Aspergillus niger* is preferred. The use of an endoglucanase originating in *Trichoderma reesei* or an endoglucanase originating in *Aspergillus niger* is even more preferred. The endoglucanase belonging to GHF5 can either be used alone or in a suitable combination of two or more types thereof.

Endoglucanases belonging to GHF12 can be noted as the endoglucanase. Among these, an endoglucanase originating in *Trichoderma reesei* and an endoglucanase originating in *Aspergillus niger* and an endoglucanase originating in *Aspergillus oryzae*, can be noted. One or two or more types selected from among such endoglucanases can be suitably combined and used.

Endoglucanases belonging to GHF7 and GHF45 can also serve as the endoglucanase. Among these, the use of an endoglucanase originating in *Trichoderma reesei* and an endoglucanase originating in *Aspergillus oryzae* are preferred.

The enzyme preparation of the present teachings can also contain an endoglucanase originating in *Phanerochaete chrysosporium*. An endoglucanase originating in *Phanerochaete chrysosporium* can easily be obtained together with PcCBHII or a variant thereof when the PcCBH2 or variant thereof is obtained from the culture product of *Phanerochaete chrysosporium*.

The enzyme preparation of the present teachings can contain a different cellulase other than an endoglucanase. For example, it can contain a cellobiohydrolase (CBHI) belonging to GHF7. In the case of CBHI, an even greater synergistic effect on cellulose degradation is exhibited by the CBHI acting cooperatively with PcCBH2 and the like. The CBHI can originate in *Phanerochaete chrysosporium* or it can originate in a different source.

The enzyme preparation of the present teachings can contain two or more types of cellulases obtained from a culture product (or alternatively, the supernatant) of a cellulase-producing organism of a different source. The cellulase-producing organism is not particularly limited herein and can be suitably selected as needed, but *Trichoderma reesei, Aspergillus aculeatus, Aspergillus niger, Aspergillus oryzae* and the like can be noted as preferred sources of the endoglucanase, and *Trichoderma reesei* cand be noted as more preferred source of the same.

The enzyme preparation of the present teachings can contain β-glucosidase, or it can contain essentially no β-glucosidase. If the enzyme preparation of the present teachings contains essentially no β-glucosidase, then glucose generated by β-glucosidase does not cause product inhibition of the other cellulases, and this is preferred. Therefore, if an enzyme preparation containing essentially no β-glucosidase is used, it is possible to reliably avoid product inhibition and obtain the synergistic effect on cellulose degradation that has been verified by the authors with the aforementioned evaluation system. Such an enzyme preparation does not decompose cellulose to glucose, and it can be used for an application in which cellulose is decomposed to cellobiose and other oligomers.

Containing essentially no β-glucosidase means not only that β-glucosidase is not contained therein; it also means that an amount of β-glucosidase can be contained therein within a range enabling avoidance or control of product inhibition by β-glucosidase. The enzyme preparation of the present teachings contains no β-glucosidase. An enzyme preparation containing essentially no β-glucosidase can be easily obtained, for example, from the culture product of a transformant prepared by using genes encoding PcCBH2, etc., and an endoglucanase originating in a different source to transfect a microorganism that does not have an endogenous β-glucosidase gene (e.g., yeast, koji mold, etc.) or a microorganism that has a knocked-out endogenous β-glucosidase gene.

The enzyme preparation of the present teachings can contain respectively purified PcCBH2, etc. and an endoglucanase originating in a different source, or it can contain other proteins and other components as a crude protein product. Modes of the preparation are not particularly limited herein, and it can be a solid preparation (powder, (in lyophilized form, etc.), tablets, granules, and the like) or a liquid (preferably frozen at the time of distribution).

The process of producing the enzyme preparation of the present teachings is not particularly limited herein. For example, it may be in a mode where the endoglucanase originating in a different source (as noted above, this can be a culture product of a cellulase producing organism from a different source) and separately prepared PcCBH2, etc., are mixed together, or it can be in a mode in which it is manufactured from a culture product obtained by culturing a transformant in which PcCBH2, etc., and the endoglucanase originating in another source are co-expressed. It can also be a mode where these modes are suitably combined.

(Cellulose Degradation Activity Enhancer)

The cellulose degradation activity enhancer of the present teachings contains PcCBH2, etc., and is used by combining the same with an endoglucanase originating in a different source other than *Phanerochaete chrysosporium*. In the case of PcCBH2, etc., in the present teachings, exhibits an excellent synergistic effect on cellulose degradation in combination with an endoglucanase originating in a different source, and therefore it can assume the mode of an enhancer (additive) in which the variant is used in combination with an endoglucanase originating in a different source. The PcCBH2 and variant thereof in the enhancer of the present teachings is used in the various forms as described above. In addition, the preferred endoglucanase originating in a different source for use in the enhancer is used in the various forms of endoglucanase preferred for combination in the enzyme preparation of the present teachings. At the time of combining the enhancer of the present teachings, various forms of other cellulases preferred for combination in the enzyme preparation of the present teachings can also be used.

The enhancer of the present teachings can contain CBHI. The synergistic effect on cellulose degradation is enhanced even more by the inclusion of CBHI when it is combined with the endoglucanase originating in a different source. CBHI originating in *Phanerochaete chrysosporium* (PcCBHI) can be noted as a preferred CBHI.

The enhancer of the present teachings can contain PcCBH2, etc., that has been purified, or it can contain other proteins and other components as a crude protein product. Modes of the enhancer are not particularly limited herein, and it can be a solid preparation (powder, (in lyophilized form, etc.), tablets, granules, and the like) or a liquid (preferably frozen at the time of distribution).

The process of producing the enhancer of the present teachings is not particularly limited herein. In the case of PcCBH2 originating in nature, a microorganism producing the PcCBH2 can be cultured, etc., and the enhancer of the present teachings can be obtained as a protein fraction or part thereof. A variant can be obtained through genetic engineering methods and made into the enhancer of the present teachings. PcCBH2 originating in nature can also be obtained by genetic engineering methods.

(DNA Construct)

The DNA construct of the present teachings comprises DNA encoding the variant of the present teachings. More specifically, it comprises DNA encoding the amino acid sequence represented by SEQ ID NO: 4, and even more specifically, it comprises DNA having the base sequence represented by SEQ ID NO: 3. Furthermore, the DNA construct comprises DNA encoding the amino acid sequences of variants having one or more of amino acid mutations listed in the above Table 3 and DNA encoding the amino acid sequences of the variants listed in Table 4. The DNA construct of the present teachings can assume the mode of an expression vector intended for transformation of a host cell that is suitable as a host. The DNA construct may be employed in any of various forms depending on the manner of use. For example, the DNA construct may be used in the form of a DNA fragment, or may be used in a suitable vector form such as a plasmid or cosmid.

The present teachings not only provides a polynucleotide encoding the amino acid sequence represented by SEQ ID NO: 4 and a polynucleotide having the base sequence represented by SEQ ID NO: 3, but also a polynucleotide encoding the various forms of PcCBH2 and variants thereof. The polynucleotide may be in any suitable form, such as DNA (either double-stranded or single-stranded DNA), RNA, or a DNA/RNA hybrid.

(Transformant)

One mode of the transformant of the present teachings is a transformant expressing the variant of the present teachings, and it can be obtained by transformation of a suitable host cell with the DNA construct of the present teachings described above. For example, a transformant expressing only the variant of the present teachings in a form that is retained on the cell surface or secreted extracellularly can itself be utilized as the enhancer of the present teachings. Furthermore, a culture product obtained by culturing such a transformant can be utilized as a preferred source for obtaining the enhancer of the present teachings.

The transformant of the present teachings can assume a mode where both PcCBH2, etc., and an EG originating in a different source are co-expressed. In accordance with a transformant in such a co-expression mode, a combination enabling a synergistic effect on cellulose degradation can be obtained all at once, and this is advantageous for manufacturing the enzyme preparation and for cellulose degradation by the transformant. The various types of endoglucanase and other cellulases relating to the enzyme preparation of the present teachings and previously described can be used as the ones preferably expressed in a transformant of this mode.

The transformant of the present teachings may be obtained by transforming a suitable host cell with the above DNA construct. Any of various suitable techniques known to the art may be used for this purpose, including transformation, transfection, conjugation, protoplast fusion, electroporation, lipofection and the lithium acetate method. The cell serving as the host for gene transfer is not subject to any particular limitation. However, taking into account the subsequently described organic acid fermentation, ethanol fermentation and the like, illustrative examples of suitable cells include *Saccharomyces* yeasts such as *Saccharomyces cerevisiae*, *Schizosaccharomyces* yeasts such as *Schizosaccharomyces pombe*, *Candida* yeasts such as *Candida shehatae*, *Pichia* yeasts such as *Pichia stipitis*, *Hansenula* yeasts, *Trichosporon* yeasts, *Brettanomyces* yeasts, *Pachysolen* yeasts, *Yamadazyma* yeasts, and *Kluveromyces* yeasts such as *Kluveromyces marxianus* and *Kluveromyces lactis*.

In the preparation of the co-expression mode of the transformant, the genes to be inserted will be suitably determined in accordance with the type of host so that the enzymes will be expressed in the combination of the present teachings. For example, when *Phanerochaete chrysosporium* is used as the host, the PcCBH2 gene is endogenous, and therefore an endoglucanase gene originating in *Trichoderma reesei*, for example, can be inserted for the endoglucanase originating in a different source. On the other hand, when *Trichoderma reesei* is used as the host, the gene of the endoglucanase originating in a different source is endogenous, so a foreign gene encoding PcCBH2, etc., is inserted. Additionally, foreign genes encoding the PcCBH2, etc., and the endoglucanase gene originating in a different source can each be inserted into an organism that does not produce cellulase.

In the transformant of the present teachings a cellulase gene other than the preferred combination of the present teachings can also be expressed, or the expression thereof can be inhibited. By inhibiting expression of a cellulase gene other than the preferred combination, only the necessary proteins will be expressed in large quantity, and cellulose can be efficiently decomposed by the synergistic effect on cellulose degradation due to the combination of the present invention. Such a transformant is advantageous for manufacturing an enzyme preparation that can exhibit a powerful synergistic effect.

For example, when a foreign gene encoding PcCBH2, etc., is inserted into *Trichoderma reesei* to obtain the transformant of the present invention, the CBHI and CBHII of *Trichoderma reesei* can be expressed, or these genes can be knocked out to inactivate them. Alternatively, the transformant of the present invention can be obtained by inserting a foreign gene encoding an enzyme of the preferred combination of the present invention into organism that does not produce cellulase selected from yeast and koji mold. As described below, an organism that does not produce cellulase has the merits of not having an endogenous β-glucosamine gene, thereby enabling control of the amount of PcCBH2, etc., and endoglucanase inserted as foreign genes thereinto to obtain a high level of expression. Such a transformant is advantageous for manufacturing an enzyme preparation that can exhibit a powerful synergistic effect.

It is preferable for the expression of β-glucosidase to be inhibited in the transformant of the present invention. In other words, a preferred transformant utilizes a host with an endogenous β-glucosidase gene wherein that gene has been knocked out, or utilizes a host without an endogenous β-glucosidase gene (for example, an organism that does not produce cellulase). As previously noted, this is because β-glucosidase inhibits cellulose degradation through product inhibition. Such a transformant is preferred as the enzyme preparation, particularly the enzyme preparation for breaking down cellulose to low molecular weight oligomers. A person skilled in the art can suitably knock out the specific gene.

The above-described polynucleotide, DNA construct and transformant of the present teachings may be prepared by methods carried out in general accordance with processes described in, for example, *Molecular Cloning, 3rd and Current Protocols in Molecular Biology*.

In the transformant of the present invention, such a combination of enzymes can be expressed intracellularly, or it can be configured to be retained on the cell surface or secreted extracellularly. The transformant can be utilized unchanged for cellulose degradation in a mode wherein the enzymes are retained on the cell surface or secreted extracellularly. The mode wherein the enzymes are secreted extracellularly is advantageous for acquiring the enzyme preparation from the culture supernatant.

(Process for Producing Enzyme Preparation)

The present invention provides a process for producing the enzyme preparation of the present invention using a co-expression transformant of the present invention. In accordance with the present invention, an enzyme preparation consisting of the preferred combination of cellulases can be obtained all at once. In the production process of the present invention an efficient and powerful enzyme preparation can be easily obtained, especially by using a transformant considered preferable for production of the enzyme preparation from among the aforementioned co-expression transformants.

The culturing conditions of the transformant are suitably determined in consideration of the host, expression vector, and the like to be used. The cultured cells and/or culture supernatant can be obtained from the culture, the fraction containing proteins can be obtained therefrom, and if necessary, the proteins can be isolated and purified. Publicly known protein isolation and purification methods can be used therefor. When the PcCBH2 and endoglucanase originating in a different source are produced and secreted, the culture supernatant therefrom can be used unchanged. The obtained enzyme fraction can be dried or powdered as needed to prepare various modes of the enzyme preparation.

When the enzyme preparation contains two or more types of cellulases obtained from the culture products (or culture supernatants) of different organisms producing a cellulase originating in a different source, these culture products can be combined and the proteins isolated therefrom, or the proteins can be isolated from such culture products separately from the co-expression transformant of the present invention and then added to the culture product of the co-expression transformant or the enzyme preparation of the present invention.

(Process for Producing Low Molecular Weight Cellulose Product)

The process for producing the low molecular weight cellulose product of the present invention provides a step in which cellulose is converted to a low molecular weight product using PcCBH2, etc., and an endoglucanase originating in a different source in the presence of cellulose. Low molecular weight cellulose, cellulose oligomers, or glucose can be produced efficiently in accordance with the present invention. To reduce the molecular weight to glucose, β-glucosidase is also used.

In the molecular weight lowering step, degrading cellulose essentially without the presence of β-glucosidase is preferred for degrading cellulose efficiently to cellulose oligomers. By so doing, the effect of product inhibition due to β-glucosidase can be avoided or controlled. The expression "essentially without the presence of β-glucosidase" means not only that β-glucosidase is not present therein; it also means that an amount of β-glucosidase can be present therein within a range that enables avoidance or control of product inhibition by β-glucosidase. Preferably, β-glucosidase is not present in an enzyme reaction system for obtaining cellulose oligomers.

The molecular weight lowering step can be made into a process wherein cellulose is decomposed using PcCBH2, etc., and an endoglucanase originating in a different source without the presence of β-glucosidase, and then β-glucosidase is supplied to decompose the cellulose oligomers obtained thereby. By so doing, cellulose can be efficiently decomposed to glucose.

PcCBH2, etc., and an endoglucanase originating in a different source (e.g., a commercially available enzyme preparation, etc.) can be combined and used in the molecular weight lowering step. An excellent synergistic effect can be exhibited thereby. For example, an excellent synergistic effect with another endoglucanase can be obtained even with a pretreated product of a lignocellulose-based biomass such as rice straw, etc., that contains cellulose, lignin, and hemicellulose. More specifically, variants 52 to 58 can exhibit an excellent synergistic effect when combined with a commercially available enzyme preparation such as a cellulase preparation, and with BGL+EG+CBHI.

The combination of the PcCBH2, etc., and the endoglucanase originating in a different source used in the production process of the present invention can be provided as the enzyme preparation of the present invention described above, or it can be provided in a form wherein the combination is presented on the cell surface of the co-expression transformant of the present invention. Furthermore, PcCBH2, etc., alone can be provided as an enzyme preparation, and the endoglucanase originating in a different source can be provided on the cell surface or in a form secreted extracellularly. Various means are known as methods for extracellular secretion and cell surface retention, but a method can be noted wherein a transformant is obtained that expresses a fusion protein wherein the PcCBH2, etc., and the endoglucanase originating in a different source are linked with a publicly known protein for cell surface display or a secretory protein.

The various forms of the combination of the present invention consisting of PcCBH2, etc., and endoglucanase originating in a different source that have already been described can be applied to the process for producing a low molecular weight cellulose product of the present invention described above. Additionally, even more efficient cellulose degradation is enabled by using a preferred mode of a combination thereof.

(Process for Producing Useful Substance)

A first step wherein cellulose oligomers are produced by degrading cellulose using PcCBH2, etc., and an endoglucanase originating in a different source in the presence of cellulose and essentially without the presence of β-glucosidase, and a second step wherein glucose is produced by degrading the above cellulose oligomers with β-glucosidase can be provided. In the process for producing a useful substance of the present invention, once the cellulose has been decomposed to cellulose oligomers, preferably those oligomers are collected, and then they are further decomposed with β-glucosidase to obtain glucose. Thus, a useful substance can be obtained by first obtaining the cellulose oligomers efficiently through avoiding or controlling inhibition of the enzyme reaction due to glucose, obtaining glucose efficiently by utilizing β-glucosidase to act on those oligomers, and then using the glucose as a carbon source therefor.

The useful substance is not particularly limited herein, but one that can be produced by a microorganism utilizing glucose is preferred. The utilizing microorganism is not particularly limited herein and, for example, it can be ethanol producing microorganism such as yeast and organic acid producing microorganism such as lactic bacterium and yeast. These microorganisms can be genetic modified. For example, microorganisms can be those modified to enable production of a compound that is not originally a metabolite thereof by using gene recombination to substitute, add, etc., one or more enzymes in a metabolic system utilizing glucose as a starting material. For example, this can be used for the production of fine chemicals (coenzyme Q10, vitamins, and starting materials therefor) by an addition to the isoprenoid synthetic pathway, for the production of glycerin by modification of the glycolytic pathway, and for the production of starting materials for plastics and chemical products in biorefinery technology.

The process for producing a useful substance of the present invention can utilize the glucose obtained in the glucose production step as a carbon source, and the glucose production step can be made into an ethanol fermentation step by degrading the aforementioned cellulose oligomers using a microorganism expressing β-glucosidase, and using the glucose obtained thereby as a carbon source. By so doing, ethanol can be efficiently produced utilizing cellulose without product inhibition by glucose. Furthermore, the glucose production step can be made into an organic acid fermentation step by degrading the aforementioned cellulose oligomers using an organic acid producing microorganism that expresses β-glucosidase, and using the glucose obtained thereby as a carbon source. By so doing, an organic acid can be efficiently produced utilizing cellulose without product inhibition by glucose.

In the present specification, "organic acid" refers to organic compounds which exhibit acidity, and are either free acids or their salts. The acidic group in such an "organic acid" is preferably a carboxyl group. Illustrative examples of such "organic acids" include lactic acid, butyric acid, acetic acid, pyruvic acid, succinic acid, formic acid, malic acid, citric acid, malonic acid, propionic acid, ascorbic acid and adipic acid. These "organic acids" may be the stereoisomeric D-form, L-form or DL-form. The "organic acid" is preferably lactic acid, An example of a method for displaying the protein at the surface of yeast cells involves transforming yeast so that it expresses a fused protein obtained by linking a protein for cell surface display or a secretory protein with the protein of the present teachings. The yeast serving as the host in the surface-displaying yeast is not subject to any particular limitation, although the yeast described above in the "Transformant" section may be advantageously used in the same way here. Moreover, because surface display enables the cellulose to be directly saccharified and utilized, the host of the surface-displaying yeast is preferably a transformant that has been transformed so as to produce a useful substance or a variant. Such transformants, although not subject to any particular limitation, are exemplified by, for lactic acid fermentation, the lactic acid-producing yeasts disclosed in Japanese Patent Application Laid-open Nos. 2003-259878, 2004-18763, 2005-137306, 2006-6271, 2006-20602, 2006-42719, 2006-28318, 2006-296377, 2007-89466 and 2007-175029. However, use is not limited to such transformants as the host for inducing the production of a useful substance in the surface-displaying yeast of the present teachings. The desired useful substance may instead be produced by carrying out some other transformation on the surface-displaying yeast that has been prepared.

The various forms of the combination of the present invention consisting of PcCBH2, etc., and endoglucanase originating in a different source that have already been described can be applied to the process for producing a useful substance of the present invention described above. Additionally, even more efficient cellulose degradation is enabled by using a preferred mode of a combination thereof.

The present teachings is described more fully in the following examples, which are illustrative and should not be construed as limiting the present teachings. The gene recombinations described below were carried out in accordance with *Molecular Cloning. A Laboratory Manual*, by T. Maniatis, et al. (Cold Spring Harbor Laboratory).

Example 1

Production of Active Forms of Various Cellulases

The group of enzymes that cleave glycoside bonds (EC 3.2.1.-) are classified according to their Glycoside Hydrolase Family (hereinafter, GHF), and various cellulases are included therein. To test the synergistic effects of CBH and EG enzymes belonging to as many GHFs as possible were evaluated in this example. The following have been reported: CBH (EC 3.2.1.91) classified into GHFs 5, 6, 7, 9, 10, and 48; EG (EC 3.2.1.4) classified into GHFs 5, 6, 7, 8, 9, 10, 12, 26, 44, 45, 48, 51, 61, and 74; and BGL (EC 3.2.21) classified into GHFs 1, 3, and 9. CBH belonging to GHFs 5, 6, 7, and 9 are known. Therefore, 13 types of CBH originating in 5 species of microorganisms (*Trichoderma reesei, Phanerochaete chrysosporium, Aspergillus aculeatus, Aspergillus oryzae,* and *Clostridium thermocellum*) belonging to those 4 GHFs were used. Twenty-four types of EG originating in 6 species of microorganisms (*Trichoderma reesei, Phanerochaete chrysosporium, Aspergillus aculeatus, Aspergillus oryzae, Hemicola insolens, Clostridium thermocellum,* and *Chaetomium globosum*) and belonging to 9 GHFs, i.e., 5, 6, 7, 8, 9, 12, 45, 48, and 61 were used. One type of enzyme originating in *Phanerochaete chrysosporium* and belonging to GHF3 was used as the BGL.

A start codon, T7 promoter, and ribosome binding site (rbs) were inserted upstream of the mature protein region of each type of cellulase by PCR. A T7 terminator was inserted downstream thereof by PCR. An ethanol precipitate of the full length PCR product was used as a template for the transcription/translation reaction. For preparation of the DNA templates, a PCR primer was designed for each enzyme from DNA base sequences encoding the following enzymes that were obtained from the NCBI home page (www.ncbi.nlm.nih.gov/) according to the respective accession numbers listed below.

PcCBH II: S76141
TrCBH II: M16190
AoCBH II: AP007169
PcCBH I: M22220
TrCBH I: X69976
AaCBH I: AB002821
AoCBH I: AB089436
TrEG I: AAA34212.1
TrEG V: Z33381
AnEG II: AF331518
AoEGII: AB195229
TrEG II: AAA34213.1
AnEGIII: AJ224451
PcEG III: AY682744
TrEG III: BAA20140

After *E. coli* cells with a high level of chaperone (DnaK/DnaJ, GrpE, GroEL/GroES) were disrupted, the S30 fraction prepared without the addition of a reducing agent (dithiothallate, DTT) was used as a liquid extract (medium) for cell-free synthesis. The above template DNA, 56.4 mM Tris-acetate pH 7.4, 1.2 mM ATP, 1 mM GTP, 1 mM CTP, 1 mM UTP, 40 mM creatine phosphate, 0.7 mM 20-amino acid mix, 4.1% (w/w) polyethylene glycol-6000, 35 µg/mL folic acid, 0.2 mg/mL *E. coli* tRNA, 36 mM ammonium acetate, 0.15 mg/mL creatine kinase, 10 mM magnesium acetate, 100 mM potassium acetate, 10 µg/mL rifampicin, 7.7 µg/mL T7 RNA polymerase and fungus PDI, and 1 mM GSH/0.1 mM GSSG were added to the liquid extract, and a transcription/translation coupled reaction was carried at 26° C. for 1 to 3 hours.

For each of these enzymes a cellulose-containing plate was prepared by adding carboxylated methylcellulose to agar and solidifying the same. To an array on each cellulose-containing plate 1 µL of each reaction liquid after cell-free synthesis was added, and an enzymatic reaction was carried out. After the reaction, staining was carried out by dripping a liquid stain (Congo red) onto the cellulose-containing plate to cover the same, and a decolorization reaction was carried out until halos decolorized by the cellulase reaction areas were formed. Because halos were detected in all of the reaction liquids, it was found that CBH can be synthesized in active form with the cell-free synthesis system of Example 1.

Example 2

Evaluation of Synergistic Effect 1

In this example the degradation of insoluble cellulose by each type of cellulase synthesized by the cell-free synthesis system in Example 1 was evaluated based on the synergistic effect thereof. More specifically, 0.1% phosphoric acid swollen cellulose (hereinafter, PSC) was added to agar on a microtiter plate and solidified to make a plate containing polymeric insoluble cellulose. Next 1 µL each of the active form of BGL synthesized in Example 1 was added to all of the spots. Then 1 µL each of the active forms of CBH and EG synthesized in Example 1 was added both vertically and horizontally. Following a reaction at 40° C., staining was carried out by dripping a liquid stain (Congo red) onto the agar to cover the same, the cellulase reaction areas were decolorized, and the decolorization reaction was carried out until halos were formed (the greater the size of the decolorized white part, the higher the cellulose degradation activity). The sizes of the formed halos were measured and expressed as relative activity. PSC is a polymeric cellulose, and this is an evaluation system wherein a halo is formed only if a strong synergistic effect is found. The results are shown in FIG. 1.

As shown in FIG. 1, in the cases wherein CBHII (PcCBH2) originating in *Phanerochaete chrysosporium* was added to BGL and the various types of EG, the cellulose degradation activity was markedly higher and contribution to a synergistic effect on cellulose degradation was markedly high. The types of EG showing the strongest effects among combinations exhibiting a synergistic effect with PcCBHII were TrEGII originating in *Trichoderma reesei* and AoEGII originating in *Aspergillus oryzae* belonging to GHF5, and TrEGIII belonging to GHF 12. A high synergistic effect was also obtained with TrEGI belonging to GHF7 and TrEGV belonging to GHF45. In particular, the highest synergistic effect was exhibited by a combination of PcCBH2 and TrEGII.

Example 3

Evaluation of Synergistic Effect 2

CBHI belonging to GHF7 and CBHII belonging to GHF6 are known as forms of CBH, so it was believed preferable to add both CBHI and CBHII as the CBH added to BGL and EG. Therefore, the active form of BGL synthesized in Example 1 was prepared on the spots of plates containing polymeric insoluble cellulose prepared in the same manner as in Example 2, three types of plates spotted with 1 µL each of various combinations of CBHI and EG were prepared, and 1 µL each of a different CBHII was spotted onto each of the plates. After a reaction at 40° C., staining was carried out by dripping a liquid stain (Congo red) onto the plate to cover the same, the cellulase reaction areas were decolorized, and the decolorization reaction was carried out until halos were formed. The sizes of the formed halos were measured and expressed as relative activity. The results are shown in FIG. 2.

Figure 2A:
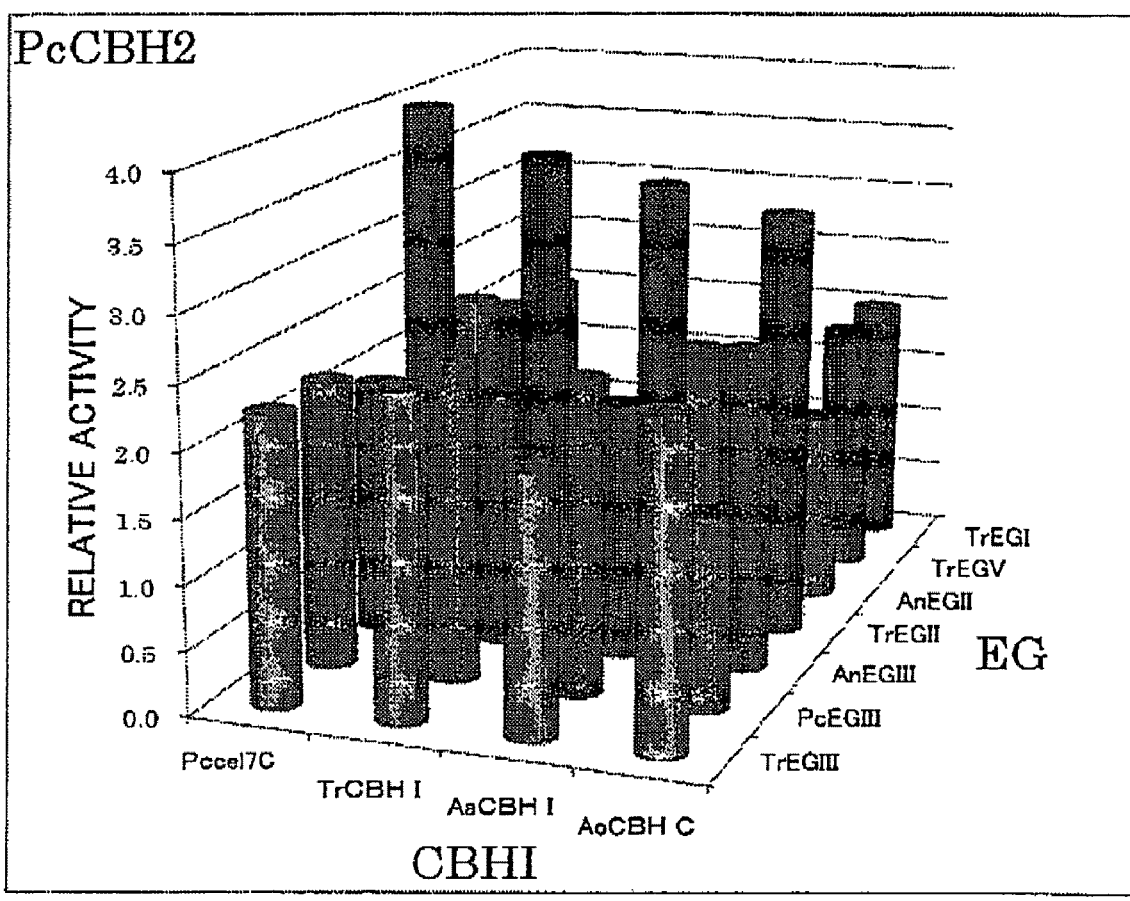
FIG. 2A is a graph showing the evaluation of the synergistic effect on cellulose degradation of PcCBHII [Note 1] in combination with various types of CBHI and endoglucanase.
Figure 2B:
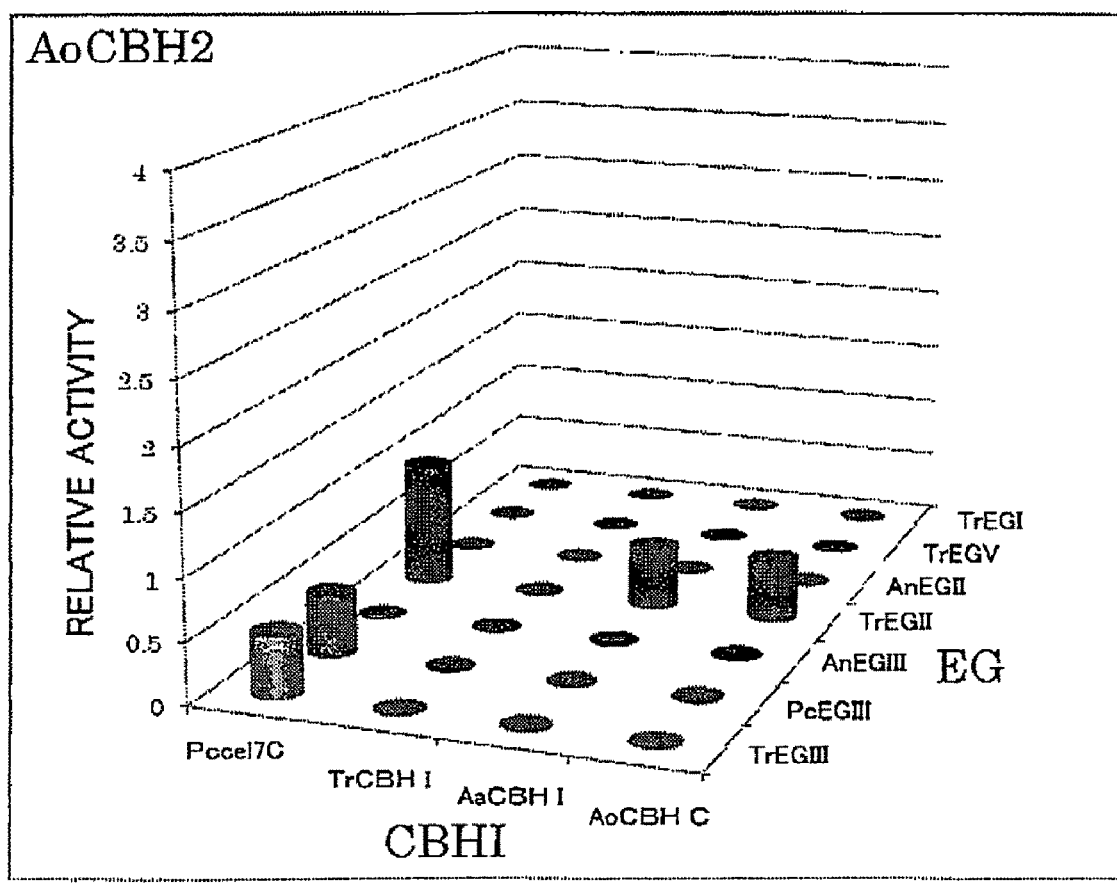
FIG. 2B is a graph showing the evaluation of the synergistic effect on cellulose degradation by AoCBHII in combination with various types of CBHI and endoglucanase.
Figure 2C:
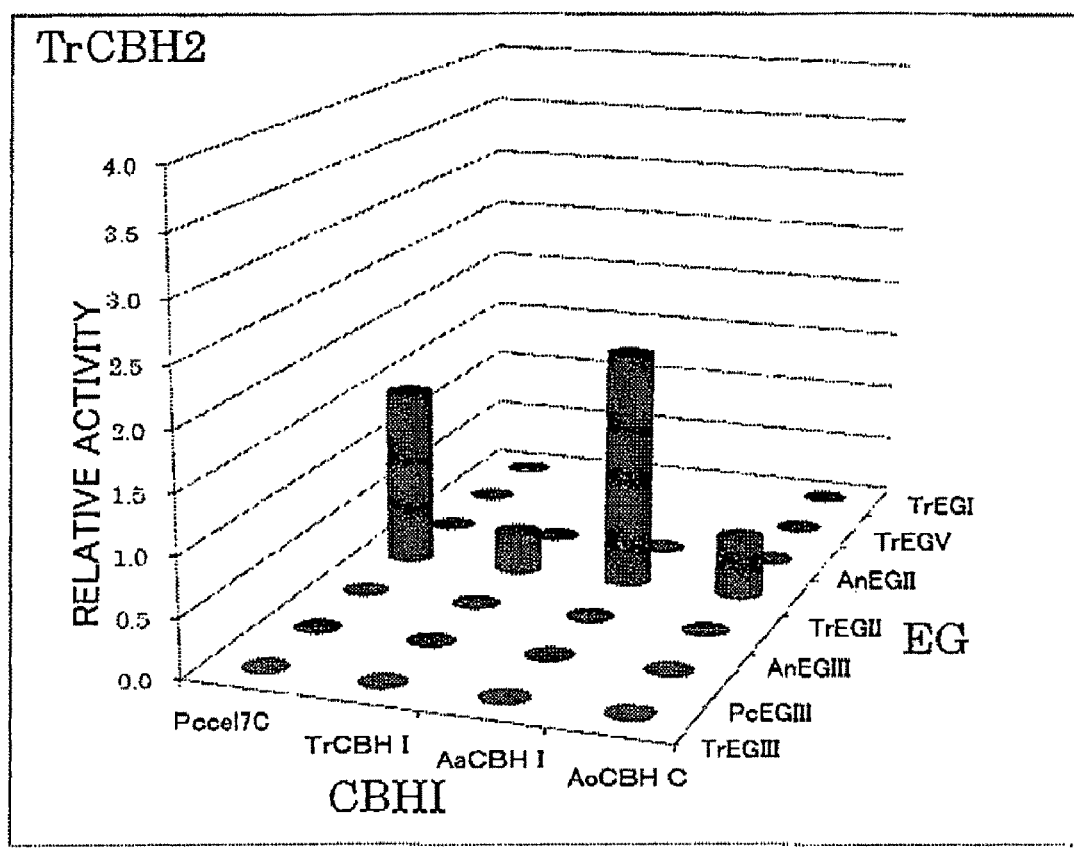
FIG. 2C is a graph showing the evaluation of the synergistic effect on cellulose degradation by TrCBHII in combination with various types of CBHI and endoglucanase.

As shown in FIG. 2A to FIG. 2C, the cellulose degradation activity was markedly higher when CBHII originating in *Phanerochaete chrysosporium* (PcCBH2) (FIG. 2A) was added than when the CBHII originating in *Trichoderma reesei* (TrCBH2) (FIG. 2C) or the CBHII originating in *Aspergillus aculeatus* (AcCBH2) (FIG. 2B) was added, and it was found that this enzyme imparted a powerful synergistic effect on cellulose degradation. The other EG forms exhibiting a synergistic effect in combination with CBHII originating in *Phanerochaete chrysosporium* were, in descending order, those belonging to GHF5 (TrEGII originating in *Trichoderma reesi* and AnEGII originating in *Aspergillus niger*), and those belonging to GHF12 (TrEGIII originating in *Trichoderma reesei*, AnEGIII originating in *Aspergillus niger* [Note 2], and PcEG IIIoriginating in *Phanerochaete chrysosporium*).

Example 4

Preparation of Variant Library

Random mutations were introduced into CBHII originating in *Phanerochaete chrysosporium*. The random mutations were amplified by error prone PCR (10 mM Tris-HCl pH 9.0, 50 mM KCl, 0.1% TRITON X-100, 5 to 10 mM $MgCl_2$, 0.5 to 2.0 mM $MnCl_2$, 0.2 mM dATP, 0.2 mM dGTP, 1 mM dCTP, 1 mM dTTP, 1 to 100 ng/μL MnP, 0.3 μM primer, 25 mU/μL Promega Taq DNA polymerase). An average of 0.5 mutations per 100 bases (error rate 0.5%) were introduced to prepare the library. After dilution to an average 1 molecule/well, single molecule PCR was carried out with LA Taq polymerase using 65 repeated cycles of heating at 94° C. for 2 min, 96° C. for 10 sec, 65° C. for 5 sec, and 72° C. for 1 min, following by heating at 72° C. for 7 min. Then 1 μL of each PCR product as a template was added to 9 μL of the cell-free protein synthesis reaction liquid with the composition shown in Example 1, and a transcription/translation coupled reaction was carried out. The variant enzyme library was constructed on six 384-well plates.

Example 5

Screening for High Activity Variants

Figure 3:
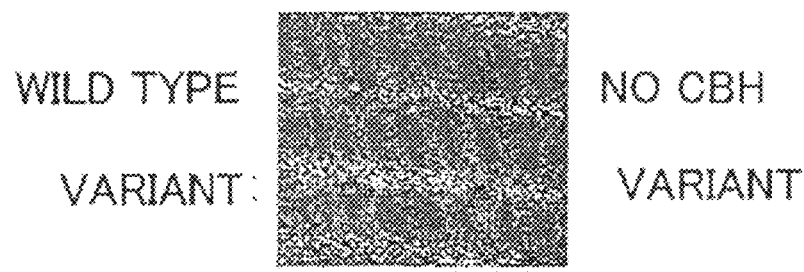
FIG. 3 is a graph showing the evaluation of the synergistic effect on cellulose degradation activity of the CBHII variant.

1 μL each from the variant enzyme library was added to polymeric insoluble cellulose containing plate containing 0.1 μL each of BGL originating in *Phanerochaete chrysosporium*, CBHI, and EGII originating in *Trichoderma reesei*, and the reaction was carried out at 40° C. As a result, wells with halos much larger than the wild type were obtained. The single molecule PCR products of the wells with the top 20 largest halos were cloned in *E. coli*, and the amino acid sequences were determined for 4 to 10 clones of transformants from each well. The clones with different sequences were selected from among the clones wherein mutations were verified, cell-free synthesis was carried out, and the degradation activity of each variant was evaluated. In the same manner as the screening, 1 μL of the synthesis product of each cloned variant was added to a plate containing polymeric insoluble cellulose spotted with 1 μL each of BGL, EG, and CBHI, and reacted at 40° C. As a result, several variants were obtained having a higher synergistic effect on cellulose degradation than the wild type. FIG. 3 shows the evaluation results for the variant with the highest effect on plates containing polymeric insoluble cellulose and exhibiting a synergistic effect (in the co-presence of BGL, EQ and CBHI).

As shown in FIG. 3, it was found that in comparison with the absence of CBH (BGL, EG, and CBHI only), the wild type PcCBH2 had a large white region, and the variant had an even larger one (approximately 2 times that of the wild type).

Example 6

Evaluation of Variant

Figure 4:
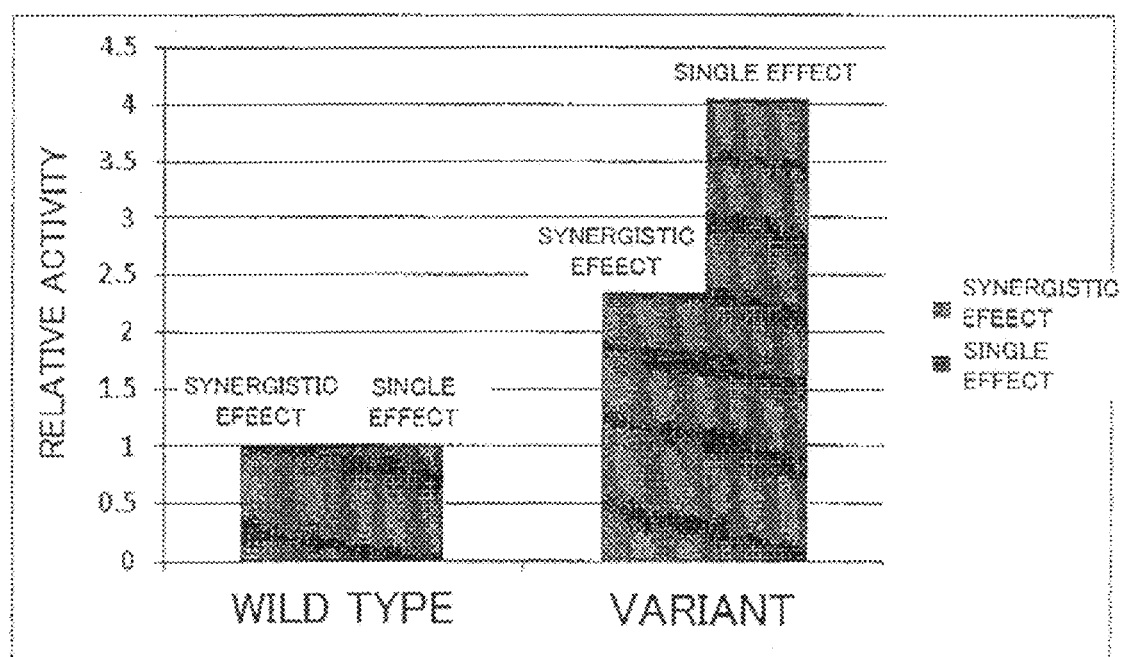
FIG. 4 is a graph showing degradation in PSC solution by the CBHII variant.

First 1 μL each of the cell-free synthesized BGL originating in *Phanerochaete chrysosporium*, the cell-free synthesized CBHI, and EGII originating in *Trichoderma reesei* was added to an aqueous solution containing 0.5% PSC and 0.5% Avicel. To that was added 1 μL each of wild type PcCBH2 and variant, and the amount of reducing sugarsafter a reaction at 40° C. for 24 hours was measured by the TZ assay (Journal of Biochemical and Biophysical Methods, 11 (1985)). FIG. 4 shows the PSC degradation activity, and FIG. 5 shows the Avicel degradation activity.

Figure 5:
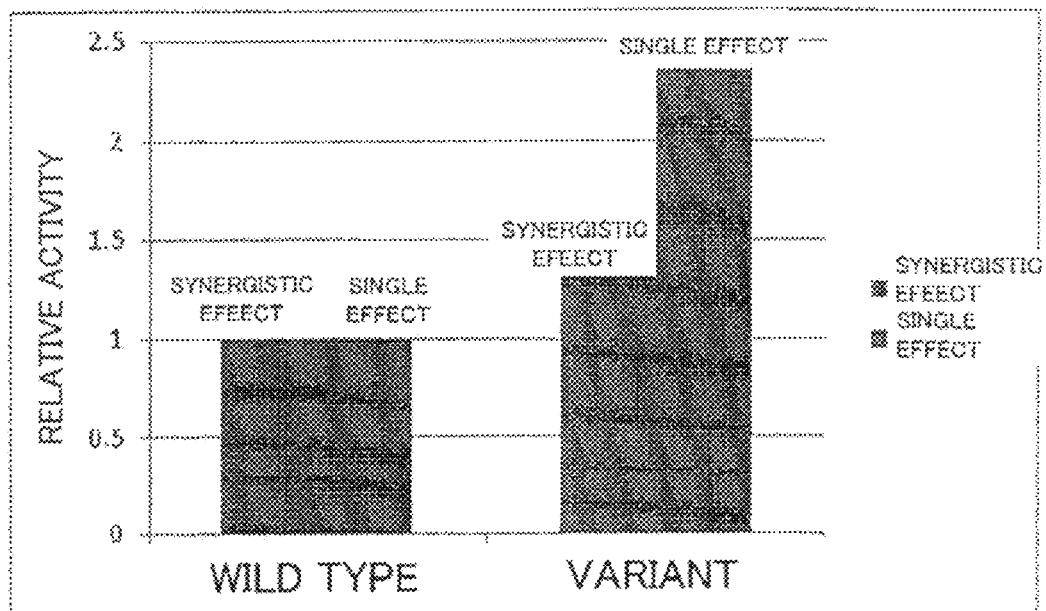
FIG. 5 is a graph showing degradation in Avicel solution by the CBHII variant.

FIG. 4 and FIG. 5 show the results of the measurement of reducing sugars in cases of PSC solution degradation alone without a synergistic effect and in cases wherein the synergistic effect was evaluated in terms of relative activity by assigning a value of 1 to wild type PcCBH2 activity. It was found that in terms of PSC degradation activity the variant had a synergistic effect 2.3 times greater than wild type PcCBH2, and the degradation activity alone was about 4 times greater. In the case of Avicel degradation activity, the synergistic effect was 1.3 times greater than wild type PcCBH2, and the degradation activity alone was 2.3 times greater. The amino acid substitution site of the variant was S22P.

Example 7

Effect of Addition to Commercial Enzyme Preparation 1

To 200 μL of 1% PSC aqueous solution was added 400 ng of Sigma Celluclast® 2730, a commercially available enzyme preparation originating in *Trichoderma reesei*, and 3 μL each of cell-free synthesized product was added in the order of wild type PcCBH2, variant, negative control (only the commercial enzyme preparation without the addition of CBH), CBHI originating in *Phanerochaete chrysosporium*, CBHI originating in *Trichoderma reesei*, CBHII originating in *Trichoderma reesei*, CBHI originating in *Aspergillus aculeatus*, and CBHI originating in *Aspergillus oryzae*, and the reaction was conducted at 40° C. The amount of reducing sugars was measured by the TZ assay shown in Example 6. The results are shown in FIG. 6.

Figure 6:
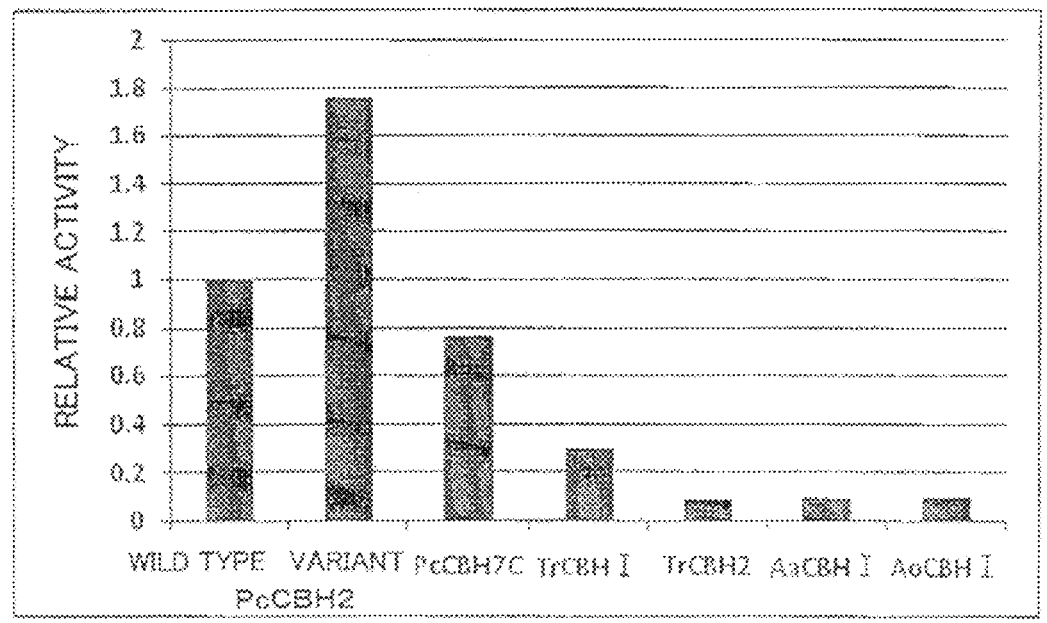
FIG. 6 is a graph showing the evaluation in PSC solution of the effect of adding PcCBH2 and the variant to a commercial enzyme preparation.

As shown in FIG. 6, the cellulose degradation activity is represented as relative activity when the wild type degradation activity is assigned a value of 1 after subtracting the value of the negative control from each. It is found that when wild type PcCBH2 was added, the degradation activity was greater than when the CBH originating in the different types of microorganisms was added. In a comparison between the wild type and the variant, the effect of adding the variant was greater.

Example 8

Expression in Yeast and Purification

Wild type PcCBH2 (CBHII originating in *Phanerochaete chrysosporium*) was amplified by PCR and subcloned to the yeast secretion expression vector pRS436GAPSSRG. The pRS436GAPSSRG vector enables secretion of an enzyme out of a cell having a secretion signal downstream from a TDH3 promoter. Yeast (strain MT8-2) were transformed by this vector and cultured for 3 days at 30° C. in SD-URA agar medium (1.7 g yeast-nitrogen base without amino acids without ammonium sulfate, 5 g casamino acids, amino acid mix, 20 g glucose, 20 g agar, 1000 mL deionized water). The culturing was carried out using a fermenter while maintaining the pH at 5.5. The grown colonies were precultured in liquid culture medium with SD-URA, then transferred into 500 ml of main culture liquid medium to obtain OD600=0.1 and cultured for 3 days at 25° C.

The culture supernatant was collected and ammonium sulfate precipitation was carried out in a concentration of 70% ammonium sulfate. After ammonium sulfate precipitation, the proteins were dissolved in buffer (IM ammonium sulfate, 0.1 M Tris (pH 7.0)), and a sample with complete buffer replacement obtained by ultrafiltration was used as the sample for purification.

An Avicel column packed with 2 mL of Avicel solution expanded with the same buffer (10 g Avicel, 40 mL buffer) was prepared. The sample was passed through the column at a flow rate of 1 mL/min using a peristaltic pump. Then a wash with 20 mL of the same buffer (flow rate 1 mL/min) was carried out followed by elution with sterile water (flow rate 0.5 mL/min). The fractions collected in 1 mL intervals were spotted onto an agar plate containing carboxymethyl cellulose, cellulose degradation activity was verified. By subjecting the fraction to SDS-PAGE, the active form of CBHII was purified to essentially a single band. The protein was quantified by a protein assay kit from BioRad.

Example 9

Effect of Addition to Commercial Enzyme Preparation 2

Figure 7:
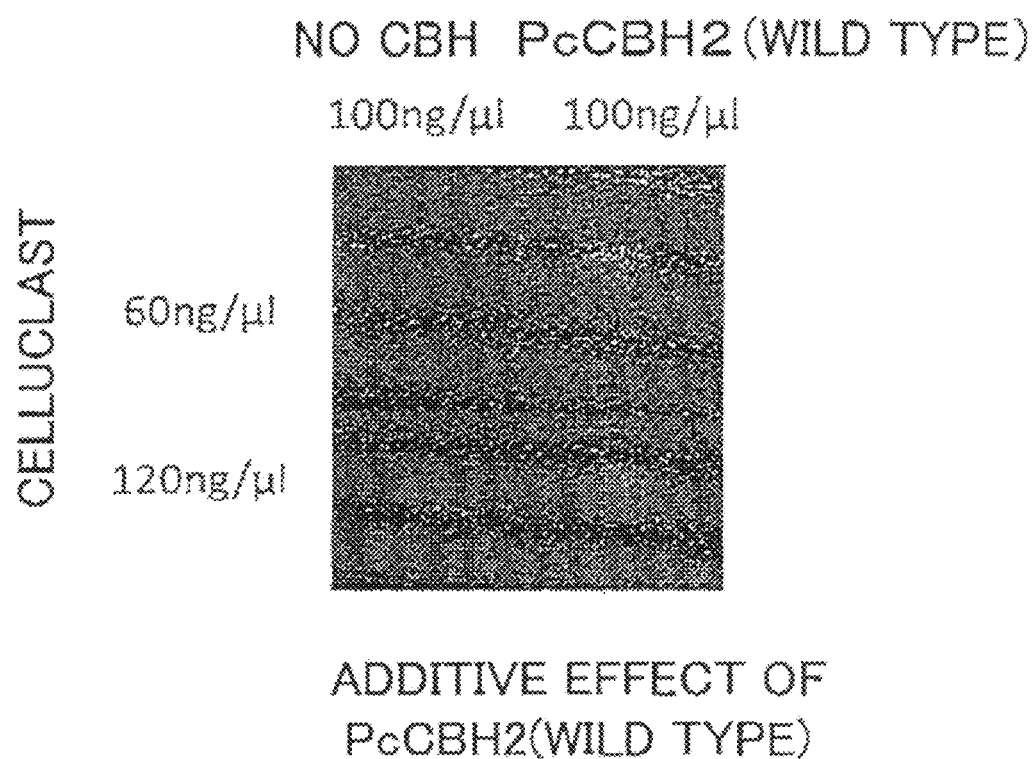
FIG. 7 is a graph showing the evaluation on a PSC plate of the effect of adding PcCBH2 to a commercial enzyme preparation.

The effect of the addition of wild type PcCBH2 obtained in Example 8 to a commercial enzyme preparation originating in *Trichoderma reesei* was evaluated. Sigma Celluclast® C2730 was used as the commercial enzyme preparation, and 1 μL each was spotted onto a plate containing 60 ng/μL of 0.1% PSC in the top row and 120 μg/μL in the bottom row. In the vertical rows starting from the left, 1 μL of negative control (no CBH), and PcCBH2 (100 ng/μL) were dripped onto the enzyme preparation spots, and the reaction was carried out at 40° C. Staining was performed with Congo red after 24 hours. FIG. 7 shows the results.

As shown in FIG. 7, it was found that the halo tends to be larger when spotted with PcCBH2 than the negative control. From the size of the halo, the degradation activity when PcCBH2 was added is approximately 1.5 to 2 times that of the negative control. Therefore, it was found that a synergistic effect that increases cellulose degradation can be obtained by adding PcCBH2 to a commercial enzyme preparation.

Example 10

Effect of Addition to Commercial Enzyme Preparation 3

Figure 8:
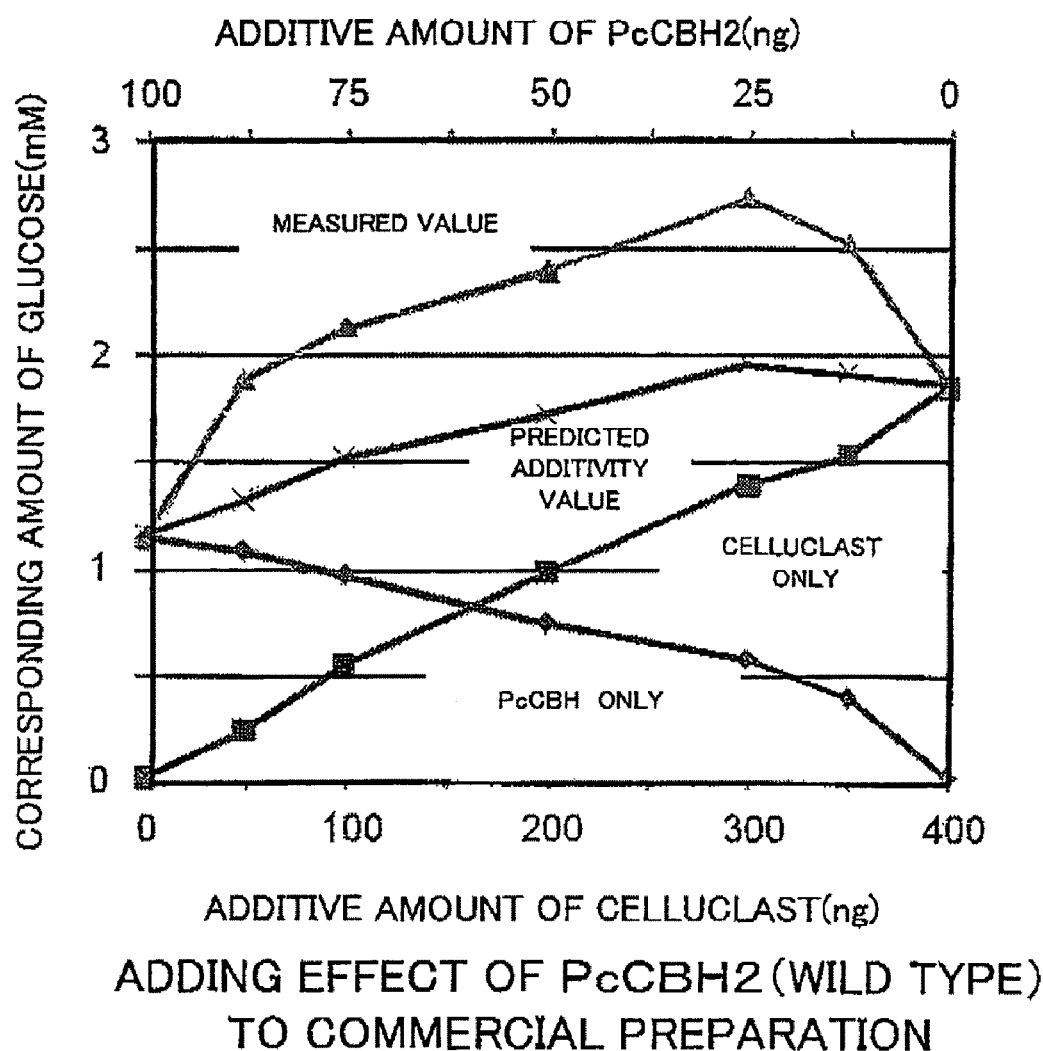
FIG. 8 is a graph showing the evaluation of the effect of adding PcCBH2 to a commercial enzyme solution with the predicted additivity values and measured values.

The effect of adding PcCBH2 to Sigma Celluclast® C2730, an enzyme preparation originating in *Trichoderma reesei*, was evaluated. To 200 μL of aqueous solution containing 1% PSC was added 1 μL each of cell-free synthesized BGL, ECA and CBHI, and then 0 to 400 ng of Celluclast® and 100 to 0 ng [Note 16] of PcCBH2 were added. The amount of reducing sugars after reaction at 40° C. for 24 hours was measured by the TZ assay (Journal [Note 2] of Biochemical and Biophysical Methods, 11 (1985)). FIG. 8 shows the predicted additivity values calculated from the activity of Celluclast® alone and PcCBH2 alone at each concentration.

As shown in FIG. 8, the measured values for PSC degradation activity were greater than the predicted additivity values, and a synergistic effect due to the addition of PcCBH2 was verified thereby. In addition, an synergetic effect was found even though the concentration of PcCBH2 was about ¼ the concentration of the added Celluclast®.

Example 11

Figure 9:
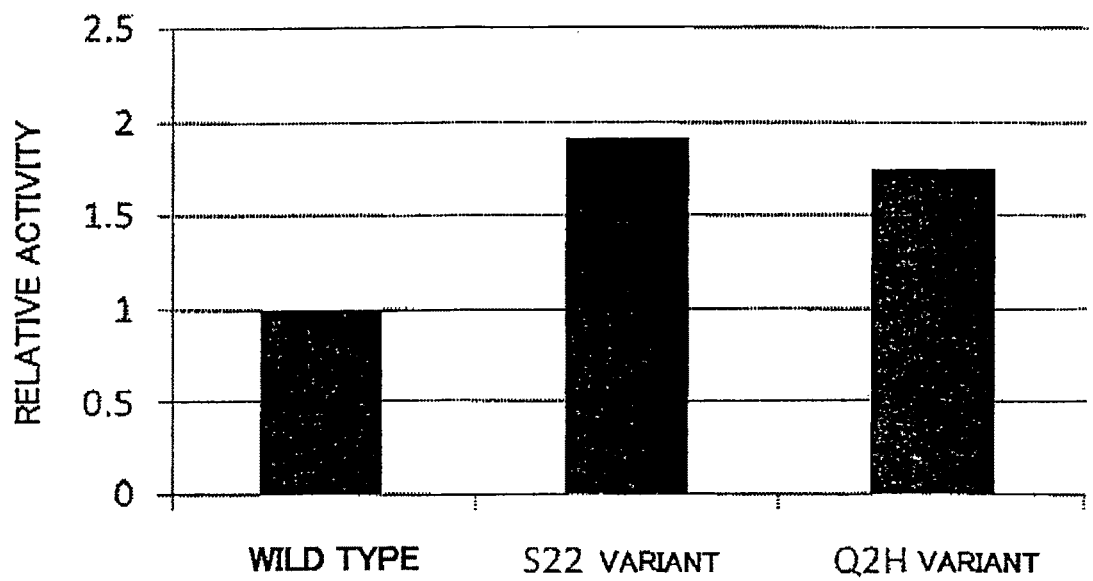
FIG. 9 is a graph showing the measured results for relative activity of the variants obtained in Example 5.

In addition to the S22P variant obtained in Example 5, the specific activity together with the amount of synthesis was measured for variant Q2H (a variant wherein the glutamine at position 2 of the amino acid sequence represented by SEQ ID NO: 2 is replaced with histidine), which had the second highest activity. For the measurement of the amount of synthesis, fluorescently labeled lysine (FLUROTECT GREENLYS in vitro Translation Labeling System: Promega) was incorporated at the time of cell-free synthesis to fluorescently label the synthesis product. It was detected using a fluorescence image analyzer (FLA9000: Fujifilm Corp.) and analysis was performed with Multi Gauge image analysis software. First 0.2 μL each of cell-free synthesized BGL, EG, and CBHI were added to an aqueous solution containing 0.5% PSC. Then, wild type PcCBH2, the S22P variant and the Q2H variant were added at an equivalent of 1 μL of wild type PcCBH2, and the reaction was carried out at 40° C. for 15 hours. The amount of reducing sugars was measured by TZ assay. FIG. 9 shows the results evaluating synergistic activity in terms of relative activity when wild type PcCBH2 was assigned a value of 1. As shown in FIG. 9, both the S22P variant and the Q2H variant exhibited a higher synergistic effect than the wild type.

Example 12

Preparation of PcCBH2 Catalytic Domain Variant Library

Random mutations were introduced using the S22P variant obtained in Example 6 as the parent gene. Amplification was carried out by error prone PCR (10 mM Tris-HCl pH 9.0, 50 mM KCL, 0.1% TRITON X-100, 5 to 10 mM $MgCl_2$, 0.5 to 2.0 mM $MnCl_2$, 0.2 mM dATP, 0.2 mM dGTP, 1 mM dCTP, 1 mM dTTP, 1 to 100 ng/μL DNA, 0.3 μM primer, 25 mU/μL Promega Taq DNA polymerase). An average of 0.5 mutations per 100 bases (error rate 0.5%) was introduced to prepare the library. Then 1 μL of each PCR product as a template was added to 7 μL of the cell-free protein synthesis reaction liquid with the composition shown in Example 1, and a transcription/translation coupled reaction was carried out. The variant enzyme library was constructed on eight 384-well plates.

Example 13

Screening Method

First 0.1 μL each of cell-free synthesized BGL, EG, and CBHI was added to 100 μL of 0.25% PSC solution, then 1 μL of each variant from the enzyme variant library was added thereto, and a reaction was carried out for 24 hr at 40° C. Centrifugal separation was performed on the reaction liquid, and the amount of reducing sugars in the supernatants obtained was measured by the Nelson-Somogyi assay. As a result, a plurality of wells wherein the amount of reducing sugars was greater than that of the S22P variant parent molecule were found. The PCR products of the top 61 wells in the amount of reducing sugars were cloned in *E. coli*, and the amount of reducing sugars was measured again by the Nelson-Somogyi assay for 4 to 10 clones of transformants from each well. The amino acid sequences of the top 60 clones therefrom were determined. The specific activity together with the amount of synthesis was measured in the same manner as in Example 11 for the clones with different amino acid sequences from among the 60 clones obtained by screening. As a result, a plurality of variants with a greater synergistic effect in specific activity than the S22P variant parent molecule.

Example 14

Evaluation Results of Variants Obtained by Screening

Figure 10:
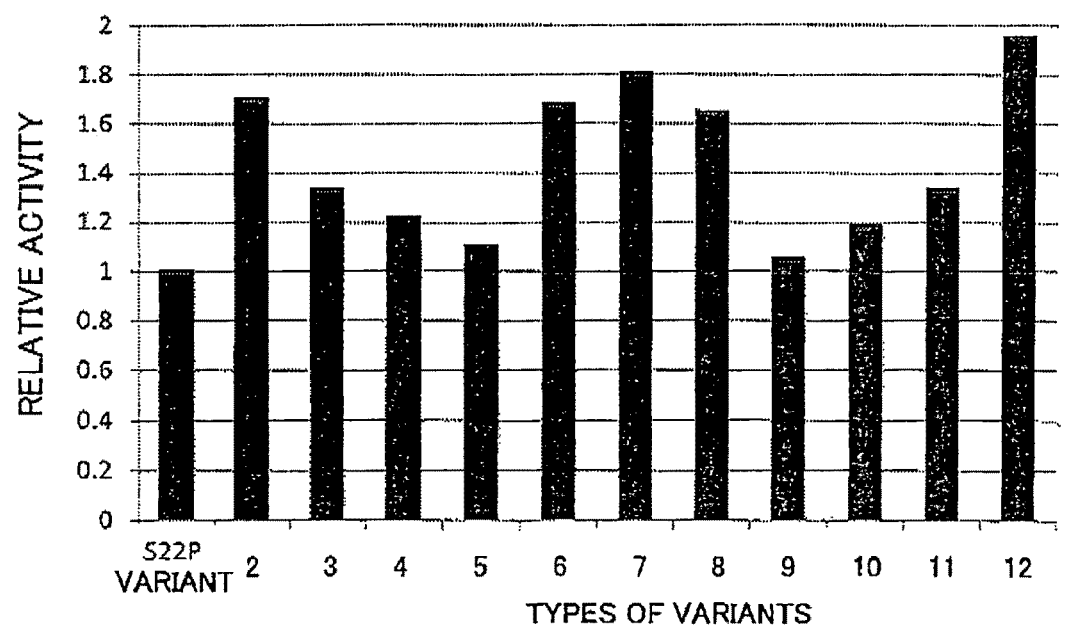
FIG. 10 is a graph showing the evaluation of the synergistic effect of the top 11 clones.

FIG. 10 shows the results of specific activity measured in the same manner as in Example 11 for the top 11 clones among the variants obtained in Example 13. As shown in FIG. 10, the PSC degradation activity in variant 12, which had the greatest activity, increased to about 2 times that of the S22P variant parent molecule due to the synergistic effect. With respect to amino acid substitutions, in addition to S22P, there were Gln2H is (Q2H), Leu29Pro (L29P) and Asn191H is (N 191H) amino acid substitutions. The Gln2H is (Q2H) mutation was at the same site as in the Q2H variant (Example 11) that had been obtained during the screening in Example 5 and had the second highest activity. Table 5 shows the amino acid substitutions of the other variants.

TABLE 5

| TYPE OF VARIANT | TYPES OF MUTATIONS | | | |
|---|---|---|---|---|
| 2 | S22P | V21I | Y32H | |
| 3 | S22P | Y32H | | |
| 4 | S22P | S60L | | |
| 5 | S22P | L132V | T298S | F382S |
| 6 | S22P | S70F | L132V | F382S |
| 7 | S22P | V28A | | |
| 8 | S22P | V21A | S69P | |
| 9 | S22P | V21A | S69P | T157S |
| 10 | S22P | N86D | P275T | L330F | F382L |
| 11 | S22P | Q2H | N191H | |
| 12 | S22P | Q2H | L29P | N191H |

Example 15

Results in Singularized Variants

Figure 11:
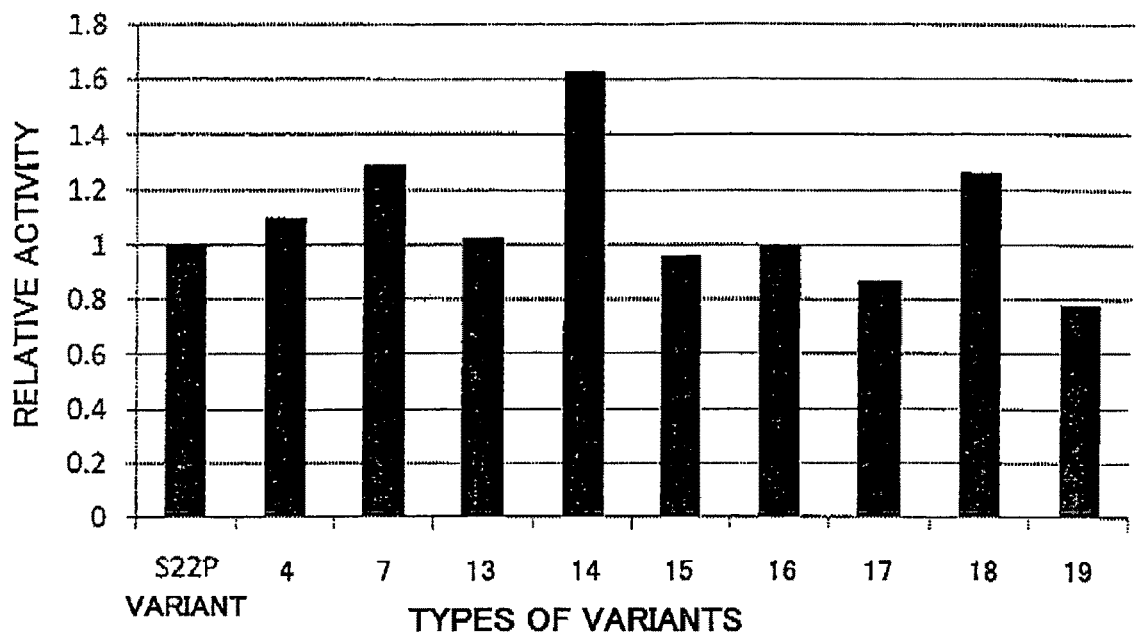
FIG. 11 is a graph showing the evaluation of the synergistic effect of singularized variants.

The effects of various mutations in comparison with the S22P variant were evaluated by isolating the mutations in clones that were variants exhibiting increased specific activity in Example 14 and having a plurality of mutations. Table 6 lists the variants that were evaluated. First 0.4 μL each of cell-free synthesized BGL, EG, and CBHI was added to 200 μL of 0.5% PSC solution and then cell-free synthesis product wherein the amount of synthesis had been measured in the same manner as in Example 11 was added thereto, and a reaction was carried out for several hours at 40° C. Centrifugal separation of the reaction liquid was performed and the amount of reducing sugars in the supernatant obtained thereby was measured by TZ assay. The results are shown in FIG. 11. Among the mutations of variants 4, 7, 14 and 18 wherein greater activity than that of the S22P variant was found, there were four mutations other than S22P that were considered effective: V28A, L29P, S60L, and N191H.

TABLE 6

| TYPE OF VARIANT | TYPES OF MUTATIONS | |
|---|---|---|
| 4 | S22P | S60L |
| 7 | S22P | V28A |
| 13 | S22P | V21A |
| 14 | S22P | L29P |
| 15 | S22P | S69P |
| 16 | S22P | S70F |
| 17 | S22P | L132V |
| 18 | S22P | N191H |
| 19 | S22P | F382S |

Example 16

Construction of PcCBH2 Three-Dimensional Model

In essence, a cellulose binding domain and a catalytic domain are present in CBH, and it is known that both assume a construction joined by linkers. The structures of both domains have been revealed by X-ray analysis, and the structures of the following two types of enzymes have been reported in the PDB (Protein Data Book) as the catalytic domain of CBHII. These are the cellotetrose complex with CBHII originating in *Trichoderma reesei* (hereinafter, TrCBH2): PDB No. 1QK2, and the cellotetraose and glucose complex with CBHII originating in *Humicola insolens*: PDB No. 2BVW. In the results of a homology search of GeneBank for only the amino acid sequence of the catalytic domain member of PcCBH2 using PSI-BLAST (Position-Specific Iterated BLAST), the top two types of sequences registered in PDB were the catalytic domains of the above CBHII enzymes. It was decided to use TrCBH2 (PDB: 1QK2), which has a higher level of homology (56%) as a reference protein for construction of the PcCBH2 model.

The display, model construction, structural stabilization calculations and the like were performed using Insight II by Accelrys. Homology modeling was performed based on alignment results of the amino acid sequences of PcCBH2 and TrCBH2 (1QK2). When the constructed model PcCBH2-CD and the main chain structure of TrCBH2 (1QK2), which was used as a reference protein at the time of model construction were overlain, the main chain structures essentially matched, and catalytic amino acid residues characteristic of CBH, a tunnel at the substrate binding site, and a loop structure at the upper part of the tunnel were found. Therefore, it was believed that a model with a certain degree of reliablity had been constructed.

Example 17

Construction of Site-Specific Variants Near the Substrate Binding Tunnel

Figure 12:
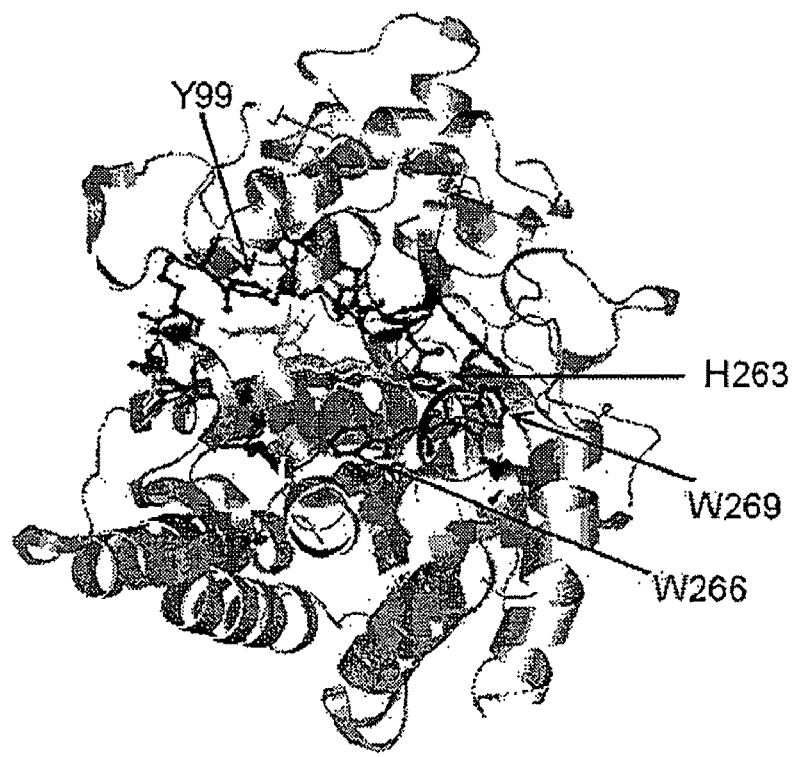
FIG. 12 is a three-dimensional structural model of PcCBH2 illustrating the insertion sites of site specific mutations.

Based on the model constructed in Example 16, it was predicted that it is possible to affect substrate binding and substrate transfer at the amino acids surrounding the cellulose chain binding tunnel. Amino acids at 17 sites that are not completely conserved in other CBH2 enzymes were selected (FIG. 12). Variants wherein these amino acid residues in wild type PcCBH2 were substituted as shown in Table 7 and the activity per amount synthesized was evaluated. In other words, 1 µL of wild type PcCBH2 and 1 µL of wild type equivalent of the various variants was added to 1% PSC to which 0.2 µL each of cell-free synthesized BGL, EG, and CBHI had been added, and after a reaction at 40° C. for 15 hours, the amount of reducing sugar was measured by TZ assay. The results are shown in FIG. 13.

TABLE 7

| NUMBER IN FIG. 13 | TYPE OF VARIANT |
| --- | --- |
| 1 | Y99A |
| 2 | Y99E |
| 3 | Y99R |
| 4 | Y99S |
| 5 | Y99W |
| 6 | Y99T(20) |
| 7 | Y99F |
| 8 | Y99M |
| 9 | D133A |
| 10 | K137A |
| 11 | K137E |
| 12 | K137R |
| 13 | K137S |
| 14 | K137W |
| 15 | K137T |
| 16 | K137F |
| 17 | K137M |
| 18 | Y166A |
| 19 | K176A |
| 20 | S178A |
| 21 | N179A |
| 22 | H263A |
| 23 | H263E |
| 24 | H263R |
| 25 | H263S |
| 26 | H263Y |
| 27 | H263T(21) |
| 28 | H263F(22) |
| 29 | H263M |
| 30 | W266A(23) |
| 31 | W266E(24) |
| 32 | W266R(25) |
| 33 | W266S(26) |
| 34 | W266Y(27) |
| 35 | W266T |
| 36 | W266F(28) |
| 37 | W266M |
| 38 | W266N(29) |
| 39 | W266Q |
| 40 | W266K |
| 41 | W266H(30) |
| 42 | W266D(31) |
| 43 | W266C |
| 44 | W266G(32) |
| 45 | W266P |
| 46 | W266I |
| 47 | W266L(33) |
| 48 | W266V |
| 49 | W269A(34) |
| 50 | W269E(35) |
| 51 | W269R(36) |
| 52 | W269S(37) |
| 53 | W269Y(38) |
| 54 | W269T(39) |
| 55 | W269F |
| 56 | W269M(40) |
| 57 | W269N(41) |
| 58 | W269Q(42) |
| 59 | W269K(43) |
| 60 | W269H(44) |
| 61 | W269D(45) |
| 62 | W269C(46) |
| 63 | W269G(47) |

TABLE 7-continued

| NUMBER IN FIG. 13 | TYPE OF VARIANT |
| --- | --- |
| 64 | W269P(48) |
| 65 | W269I(49) |
| 66 | W269L(50) |
| 67 | W269V(51) |
| 68 | N302A |
| 69 | W359A |
| 70 | W359E |
| 71 | W359R |
| 72 | W359S |
| 73 | W359Y |
| 74 | W359T |
| 75 | W359F |
| 76 | W359M |
| 77 | G360A |
| 78 | K390A |
| 79 | P391A |
| 80 | E394A |
| 81 | D407A |

NUMBERS IN BRACKETS REPRESENT NUMBERS LISTED AS TYPE OF VARIANT IN TABLE 2

FIG. 13 shows the results of the evaluation of the synergistic effect as relative activity when the activity of wild type PcCBH2 was assigned a value of 1. As shown in FIG. 13, there were 11 variants having relative activity about 2 times that of wild type PcCBH2 (23, 27, 28, 32, 34, 35, 36, 37, 39, 40, 42), 10 variants having about 1.5 times (24, 26, 31, 38, 41, 44, 45, 49, 50, 51) and 1 variants having about 1.3 times (20, 21, 22, 25, 29, 30, 33, 43, 46, 47, 48). In particular, it was found that when the amino acid residue at position 269 was substituted by an amino acid other than Trp (wild type) and Phe, the activity increased dramatically. It is surmised that amino acid residues that are hydrophobic and have an aromatic ring affect the expression of activity. In addition, Trp 266 (wild type) was the amino acid with the greatest fluctuation when the model was constructed. Because activity increased with the substitution of alanine, this indicates that it may impart stability to the expression of enzymatic activity. In addition, amino acid residue substitutions resulting in increased activity were at His 263 (H263T, H263F) and Tyr 99 (Y99T).

Example 18

Preparation of Additivity Variants

The following candidates for mutation additivity were chosen: S22P and Q2H, which were revealed to be effective mutations in Example 11, V28A, L29P, S60L and N 191H selected in Example 15, W269A, W269RX, W269M, Y99T, H263F and W266A selected in Example 17, and L132V and F382S predicted from Example 14. Among these, S22P, Q2H, L29P and N191H are all contained in variant 12. Therefore, as shown in Table 8, 7 additivity variants 52 to 58 were prepared for variant additivity based on variant 12.

TABLE 8

| TYPE OF VARIANT | TYPES OF MUTATIONS | | | | | |
| --- | --- | --- | --- | --- | --- | --- |
| 12 | S22P | Q2H | L29P | N191H | | |
| 52 | S22P | Q2H | L29P | N191H | V28A | |
| 53 | S22P | Q2H | L29P | N191H | S60L | |
| 54 | S22P | Q2H | L29P | N191H | W269M | |
| 55 | S22P | Q2H | L29P | N191H | W269M | V28A |
| 56 | S22P | Q2H | L29P | N191H | W269M | S60L |

TABLE 8-continued

| TYPE OF VARIANT | TYPES OF MUTATIONS | | | | |
|---|---|---|---|---|---|
| 57 | S22P | Q2H | L29P | N191H | W269A |
| 58 | S22P | Q2H | L29P | N191H | W269R |

Example 19

Effect of Additivity Variants in Cocktail

Figure 14:
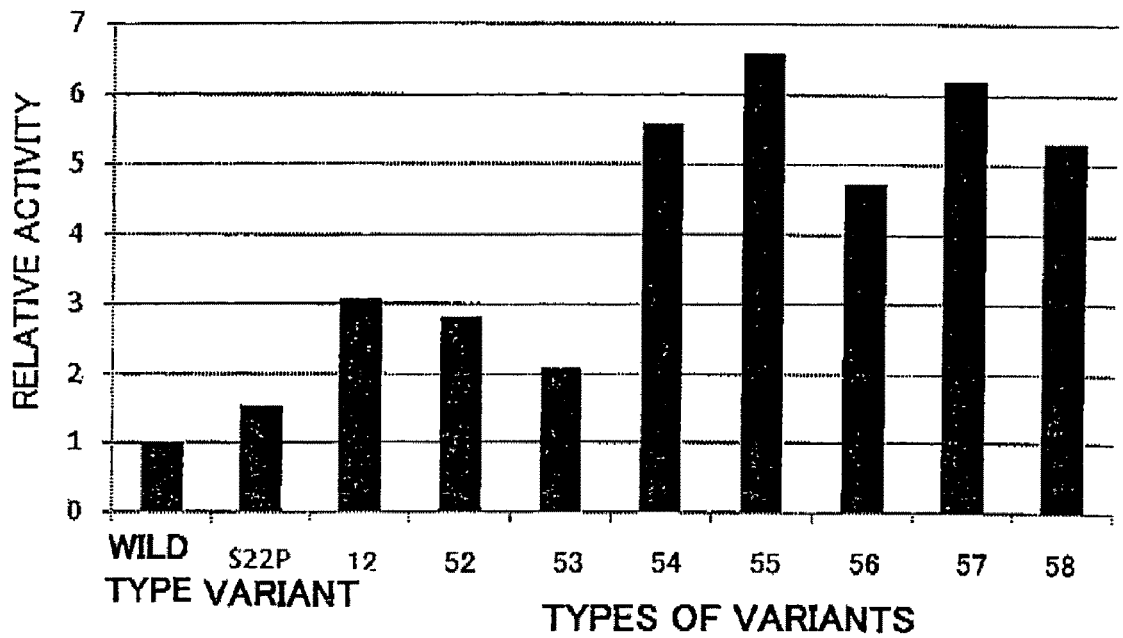
FIG. 14 is a graph showing the evaluation of the effect of adding additivity variants to the cocktail.

The cell-free synthesis product of the additivity variants shown in Table 8 wherein the amount of synthesis had been measured was added to 200 μL of 0.5% PSC solution to which 0.2 μL each of cell-free synthesized BGL, EG, and CBHI had been added, and the reaction was performed for 4 hours at 40° C. Centrifugal separation was performed on the reaction liquid, and the amount of reducing sugars in the obtained supernatant was measured by TZ assay. FIG. 14 shows the evaluation results of the synergistic effect in terms of relative activity when the activity of wild type PcCBH2 was assigned a value of 1.

In comparison with variant 12, which served as the base value for additivity, the synergistic effect in a cocktail with cell-free synthesized BGL, EG, and CBHI was increased with variants 52 to 58, and was approximately 4.5 to 6 times that of the wild type. The synergistic effect in the cocktail was highest with variant 55, which was approximately 6.5 times greater than that of the wild type. This demonstrated the possibility that activity can be increased even more by adding effective mutations together.

Example 20

Effect of Addition of Additivity Variants to Commercial Enzyme Preparation

Figure 15:
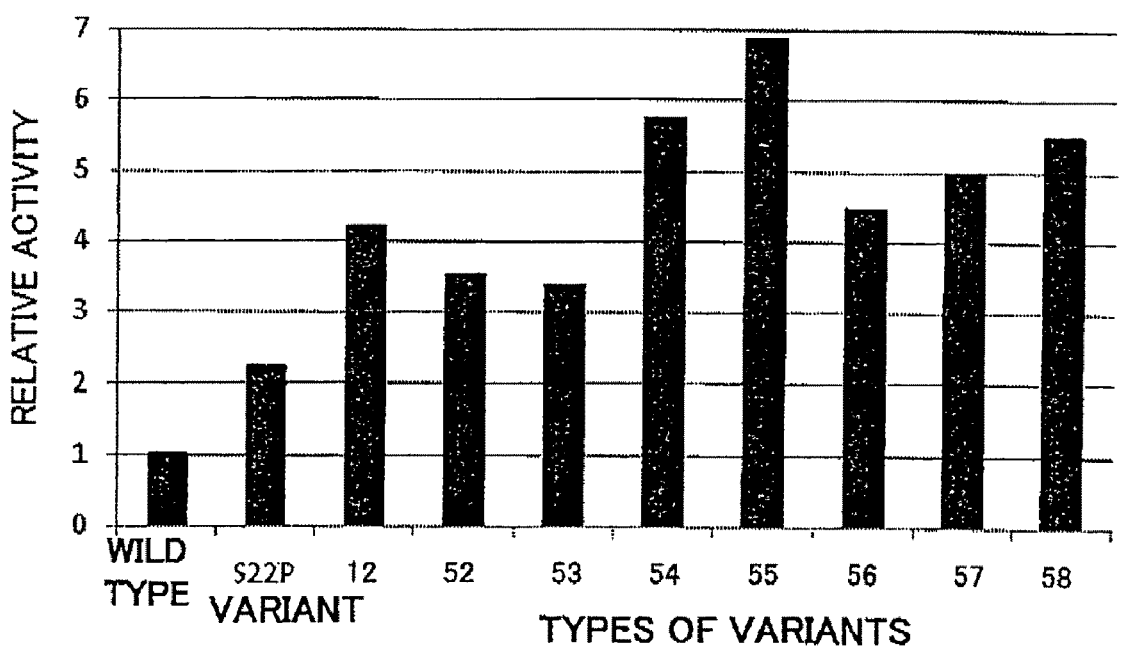
FIG. 15 is a graph showing the evaluation of the effect of adding additivity variants to a commercial enzyme preparation.

The cell-free synthesis product of the additivity variants shown in Table 9 wherein the amount of synthesis had been measured was added to 200 μL of 0.5% PSC solution to which 400 ng of commercial enzyme preparation (Sigma Celluclast® C2730) had been added, and the reaction was performed for 4 hours at 40° C. Centrifugal separation was performed on the reaction liquid, and the amount of reducing sugars in the obtained supernatant was measured by TZ assay. FIG. 15 shows the evaluation results of the synergistic effect in terms of relative activity when the activity of wild type PcCBH2 was assigned a value of 1. As shown in FIG. 15, it was found that adding variant 12 and additivity variants 54 to 58 to the commercial enzyme preparation increased the synergistic effect to approximately 3.5 to 6.5 times over that of the wild type.

Example 21

Figure 16:
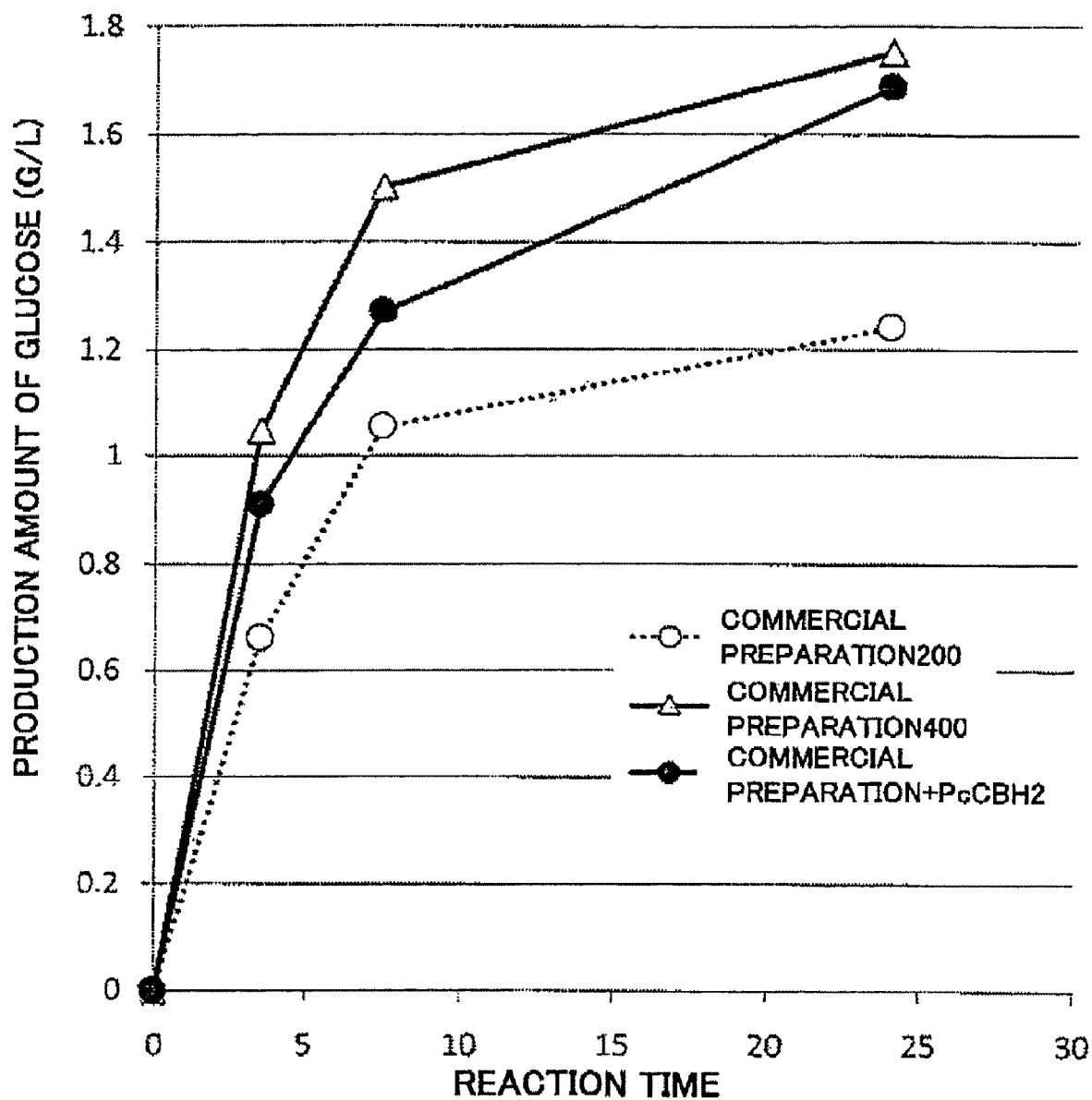
FIG. 16 is a graph showing the evaluation of the effect of adding PcCBH2 on the cellulose component from a biomass.

Synergistic Effect During Degradation of Cellulose Component from Actual Biomass by Commercial Enzyme Preparation A commercial enzyme preparation (Sigma Celluclast® C2730) was added to the cellulose component from hot-water treated rice straw to a concentration of 200 mg/g biomass (in FIG. 16: Commercial enzyme preparation 200), and after a reaction at 50° C., the glucose concentration of the solution was measured by liquid chromatography. In FIG. 16 a case wherein 2% (w/v) PcCBH2 was also added is indicated as Commercial enzyme preparation+PcCBH2. With the addition of 2% PcCBH2 alone, it was found that the amount of glucose production after 24 hours exhibited the same effectiveness as a case wherein the commercial enzyme preparation was added to a concentration of 400 mg/g biomass (in FIG. 16: Commercial enzyme preparation 400). In addition to cellulose, lignin and hemicellulose components remain in the cellulose fraction of a biomass after a simple pretreatment, so there was concern that the degradation efficiency would be lower than with a pure cellulose product, but with PcCBH2 a dramatic synergistic effect was found even in the degradation testing of the cellulose component from an actual biomass.

[Sequence Listings]

What is claimed is:

1. An enzyme preparation for cellulose degradation, comprising:
    a cellobiohydrolase comprising an amino acid sequence having at least 90% sequence identity with the amino acid sequence of SEQ ID NO: 2 or the amino acid sequence of SEQ ID NO: 4; and
    a non-*Phanerochaete chrysosporium* endoglucanase of glycoside hydrolase family 5, glycoside hydrolase family 7, glycoside hydrolase family 12, or glycoside hydrolase family 45.

2. The enzyme preparation of claim 1, wherein the cellobiohydrolase has a S22 mutation.

3. The enzyme preparation of claim 1, further comprising a cellobiohydrolase of glycoside hydrolase family 7.

4. The enzyme preparation of claim 1, wherein the endoglucanase is a *Trichoderma reesei* endoglucanase.

5. A composition for enhancing cellulose degradation, comprising:
    an isolated cellobiohydrolase comprising an amino acid sequence having at least 90% sequence identity with the amino acid sequence of SEQ ID NO: 2 or the amino acid sequence of SEQ ID NO: 4; and an isolated non-*Phanerochaete chrysosporium* endoglucanase of glycoside hydrolase family 5, glycoside hydrolase family 7, glycoside hydrolase family 12, or glycoside hydrolase family 45.

6. An isolated protein comprising the amino acid sequence of SEQ ID NO: 4, wherein said protein has cellulose degradation activity.

7. A process for degrading cellulose, comprising:
    contacting cellulose with the enzyme preparation of claim 1; and
    degrading the cellulose to a low molecular weight product.

8. A process for producing glucose, comprising:
    contacting cellulose with the enzyme preparation of claim 1;
    degrading the cellulose to obtain cellulose oligomers; and
    degrading the cellulose oligomers by contacting the cellulose oligomers with β-glucosidase to obtain glucose.

9. The process of claim 8, wherein the cellulose oligomers are degraded in the presence of an ethanol-producing microorganism that expresses β-glucosidase and the glucose is used as a carbon source by the microorganism to produce ethanol.

10. The process of claim 8, wherein the cellulose oligomers are degraded in the presence of an organic acid-producing microorganism that expresses β-glucosidase and the glucose is used as a carbon source by the microorganism to produce an organic acid.

11. An isolated protein comprising an amino acid sequence having at least 90% sequence identity with the amino acid sequence of SEQ ID NO: 2, wherein the protein has at least one mutation selected from the group consisting of S22P, Q2H, L29P, N191H, V28A, W266Y, W266F, W269A, W269R, and W269M.

12. The enzyme preparation of claim 1, wherein the cellobiohydrolase comprises an amino acid sequence having at least 95% sequence identity with the amino acid sequence of SEQ ID NO: 2 or the amino acid sequence of SEQ ID NO: 4.

13. The composition of claim 5, wherein the cellobiohydrolase comprises an amino acid sequence having at least 95% sequence identity with the amino acid sequence of SEQ ID NO: 2 or the amino acid sequence of SEQ ID NO: 4.

14. The enzyme preparation of claim 1, wherein the cellobiohydrolase comprises the amino acid sequence of SEQ ID NO: 2.

15. The enzyme preparation of claim 1, wherein the cellobiohydrolase comprises the amino acid sequence of SEQ ID NO: 4.

16. The composition of claim 5, wherein the cellobiohydrolase comprises the amino acid sequence of SEQ ID NO: 2.

17. The composition of claim 5, wherein the cellobiohydrolase comprises the amino acid sequence of SEQ ID NO: 4.

18. The isolated protein of claim 11, wherein the protein comprises an amino acid sequence having at least 95% sequence identity with the amino acid sequence of SEQ ID NO: 2.

* * * * *

```
SEQUENCE LISTING

<160> NUMBER OF SEQ ID NOS: 4

<210> SEQ ID NO 1
<211> LENGTH: 1326
<212> TYPE: DNA
<213> ORGANISM: Phanerochaete chrysosporium
<220> FEATURE:
<221> NAME/KEY: CDS
<222> LOCATION: (1)..(1326)

<400> SEQUENCE: 1 atg cag gcg tcg gag tgg gga cag tgc ggt ggc att ggt tgg act ggc      48
Met Gln Ala Ser Glu Trp Gly Gln Cys Gly Gly Ile Gly Trp Thr Gly
1               5                   10                  15 ccg acc act tgc gtc tcc ggt act acc tgc acg gtt ctc aat cca tac      96
Pro Thr Thr Cys Val Ser Gly Thr Thr Cys Thr Val Leu Asn Pro Tyr
            20                  25                  30 tac tcg cag tgc ttg cct gga tct gcg gtc acg acc tcc gtt atc         144
Tyr Ser Gln Cys Leu Pro Gly Ser Ala Val Thr Thr Thr Ser Val Ile
        35                  40                  45 acc agc cac tcg tcg tct gta tcc agc gta tcc tcg cat tcg ggc tct     192
Thr Ser His Ser Ser Ser Val Ser Ser Val Ser Ser His Ser Gly Ser
    50                  55                  60
```

| | | | | | | | | | | | | | | | | |
|---|---|---|---|---|---|---|---|---|---|---|---|---|---|---|---|---|
| tcc | act | tcg | act | tct | tct | ccc | acg | gga | cct | act | ggc | acc | aac | cct | cct | 240 |
| Ser | Thr | Ser | Thr | Ser | Ser | Pro | Thr | Gly | Pro | Thr | Gly | Thr | Asn | Pro | Pro | |
| 65 | | | | 70 | | | | | 75 | | | | | 80 | | |
| cct | cct | ccg | tcg | gct | aac | aac | ccc | tgg | act | ggc | ttc | cag | atc | ttc | ctc | 288 |
| Pro | Pro | Pro | Ser | Ala | Asn | Asn | Pro | Trp | Thr | Gly | Phe | Gln | Ile | Phe | Leu | |
| | | | | 85 | | | | | 90 | | | | | 95 | | |
| agc | cct | tac | tac | gcg | aac | gag | gtc | gcc | gct | gct | gct | aag | cag | atc | acg | 336 |
| Ser | Pro | Tyr | Tyr | Ala | Asn | Glu | Val | Ala | Ala | Ala | Ala | Lys | Gln | Ile | Thr | |
| | | | 100 | | | | | 105 | | | | | 110 | | | |
| gat | ccg | act | ctg | tcc | tct | aag | gct | gcc | agc | gtt | gca | aac | atc | ccc | act | 384 |
| Asp | Pro | Thr | Leu | Ser | Ser | Lys | Ala | Ala | Ser | Val | Ala | Asn | Ile | Pro | Thr | |
| | | | 115 | | | | | 120 | | | | | 125 | | | |
| ttc | acg | tgg | ctg | gac | tct | gtc | gcg | aag | atc | cct | gat | ctc | ggc | acc | tac | 432 |
| Phe | Thr | Trp | Leu | Asp | Ser | Val | Ala | Lys | Ile | Pro | Asp | Leu | Gly | Thr | Tyr | |
| | 130 | | | | | 135 | | | | | 140 | | | | | |
| ctt | gcc | tct | gct | tct | gca | ctg | ggc | aag | agc | act | ggc | acc | aag | caa | ctc | 480 |
| Leu | Ala | Ser | Ala | Ser | Ala | Leu | Gly | Lys | Ser | Thr | Gly | Thr | Lys | Gln | Leu | |
| 145 | | | | | 150 | | | | | 155 | | | | | 160 | |
| gtg | caa | att | gtc | atc | tac | gac | ctg | ccc | gac | cgt | gac | tgc | gct | gcc | aag | 528 |
| Val | Gln | Ile | Val | Ile | Tyr | Asp | Leu | Pro | Asp | Arg | Asp | Cys | Ala | Ala | Lys | |
| | | | | 165 | | | | | 170 | | | | | 175 | | |
| gcc | tcc | aac | gga | gag | ttc | agc | att | gcc | aac | aac | gga | caa | gcc | aac | tac | 576 |
| Ala | Ser | Asn | Gly | Glu | Phe | Ser | Ile | Ala | Asn | Asn | Gly | Gln | Ala | Asn | Tyr | |
| | | | 180 | | | | | 185 | | | | | 190 | | | |
| gag | aac | tac | atc | gac | cag | att | gtt | gct | cag | att | caa | cag | ttc | cct | gat | 624 |
| Glu | Asn | Tyr | Ile | Asp | Gln | Ile | Val | Ala | Gln | Ile | Gln | Gln | Phe | Pro | Asp | |
| | | | 195 | | | | | 200 | | | | | 205 | | | |
| gtc | cgc | gtc | gtt | gct | gtg | atc | gag | ccc | gac | tca | ctc | gcg | aac | ctg | gtc | 672 |
| Val | Arg | Val | Val | Ala | Val | Ile | Glu | Pro | Asp | Ser | Leu | Ala | Asn | Leu | Val | |
| | 210 | | | | | 215 | | | | | 220 | | | | | |
| acc | aac | ctg | aac | gtc | cag | aag | tgc | gcc | aac | gcc | aag | acg | acc | tac | ctt | 720 |
| Thr | Asn | Leu | Asn | Val | Gln | Lys | Cys | Ala | Asn | Ala | Lys | Thr | Thr | Tyr | Leu | |
| 225 | | | | | 230 | | | | | 235 | | | | | 240 | |
| gcc | tgc | gtg | aac | tac | gcg | ctc | acc | aac | ctt | gcc | aag | gtt | ggc | gtg | tac | 768 |
| Ala | Cys | Val | Asn | Tyr | Ala | Leu | Thr | Asn | Leu | Ala | Lys | Val | Gly | Val | Tyr | |
| | | | | 245 | | | | | 250 | | | | | 255 | | |
| atg | tac | atg | gat | gct | ggc | cac | gcc | ggc | tgg | ctc | ggc | tgg | ccc | gcg | aac | 816 |
| Met | Tyr | Met | Asp | Ala | Gly | His | Ala | Gly | Trp | Leu | Gly | Trp | Pro | Ala | Asn | |
| | | | 260 | | | | | 265 | | | | | 270 | | | |
| ctg | tcg | ccc | gcc | gcc | cag | ctc | ttc | acc | cag | gtc | tgg | cag | aac | gcc | ggc | 864 |
| Leu | Ser | Pro | Ala | Ala | Gln | Leu | Phe | Thr | Gln | Val | Trp | Gln | Asn | Ala | Gly | |
| | | 275 | | | | | 280 | | | | | 285 | | | | |
| aag | tct | cca | ttc | atc | aag | ggt | ctc | gcg | acc | aac | gtc | gcg | aac | tac | aac | 912 |
| Lys | Ser | Pro | Phe | Ile | Lys | Gly | Leu | Ala | Thr | Asn | Val | Ala | Asn | Tyr | Asn | |
| | 290 | | | | | 295 | | | | | 300 | | | | | |
| gcc | ctc | cag | gcc | gcg | tca | ccc | gac | ccc | atc | acg | cag | ggc | aac | ccc | aac | 960 |
| Ala | Leu | Gln | Ala | Ala | Ser | Pro | Asp | Pro | Ile | Thr | Gln | Gly | Asn | Pro | Asn | |
| 305 | | | | | 310 | | | | | 315 | | | | | 320 | |
| tat | gac | gaa | atc | cac | tac | atc | aac | gca | ctc | gcg | ccc | ttg | ctc | cag | cag | 1008 |
| Tyr | Asp | Glu | Ile | His | Tyr | Ile | Asn | Ala | Leu | Ala | Pro | Leu | Leu | Gln | Gln | |
| | | | | 325 | | | | | 330 | | | | | 335 | | |
| gcg | ggc | tgg | gac | gcg | acc | ttc | atc | gtc | gac | cag | ggc | cgc | tcc | ggt | gta | 1056 |
| Ala | Gly | Trp | Asp | Ala | Thr | Phe | Ile | Val | Asp | Gln | Gly | Arg | Ser | Gly | Val | |
| | | | 340 | | | | | 345 | | | | | 350 | | | |
| caa | aac | atc | cgc | caa | cag | tgg | ggc | gac | tgg | tgc | aac | atc | aag | ggc | gcc | 1104 |
| Gln | Asn | Ile | Arg | Gln | Gln | Trp | Gly | Asp | Trp | Cys | Asn | Ile | Lys | Gly | Ala | |
| | | | 355 | | | | | 360 | | | | | 365 | | | |
| ggc | ttc | ggt | acc | cgc | ccg | acg | acg | aac | act | ggc | tcg | cag | ttc | atc | gac | 1152 |
| Gly | Phe | Gly | Thr | Arg | Pro | Thr | Thr | Asn | Thr | Gly | Ser | Gln | Phe | Ile | Asp | |
| | 370 | | | | | 375 | | | | | 380 | | | | | |

```
tcc atc gtc tgg gtc aag ccc gga ggc gag tgc gac ggt acc tcc aac         1200
Ser Ile Val Trp Val Lys Pro Gly Gly Glu Cys Asp Gly Thr Ser Asn
385                 390                 395                 400 agc tcc tcg ccc cgc tac gac tcg act tgc tct ctg ccg gac gct gca         1248
Ser Ser Ser Pro Arg Tyr Asp Ser Thr Cys Ser Leu Pro Asp Ala Ala
            405                 410                 415 cag ccc gct cct gag gcc ggt acc tgg ttc cag gcg tac ttc cag acc         1296
Gln Pro Ala Pro Glu Ala Gly Thr Trp Phe Gln Ala Tyr Phe Gln Thr
        420                 425                 430 ctg gtt tct gct gcc aac ccg ccg ctg taa                                 1326
Leu Val Ser Ala Ala Asn Pro Pro Leu
            435                 440

<210> SEQ ID NO 2
<211> LENGTH: 441
<212> TYPE: PRT
<213> ORGANISM: Phanerochaete chrysosporium

<400> SEQUENCE: 2

Met Gln Ala Ser Glu Trp Gly Gln Cys Gly Gly Ile Gly Trp Thr Gly
1               5                   10                  15

Pro Thr Thr Cys Val Ser Gly Thr Thr Cys Thr Val Leu Asn Pro Tyr
            20                  25                  30

Tyr Ser Gln Cys Leu Pro Gly Ser Ala Val Thr Thr Thr Ser Val Ile
        35                  40                  45

Thr Ser His Ser Ser Val Ser Ser Val Ser His Ser Gly Ser
    50                  55                  60

Ser Thr Ser Thr Ser Ser Pro Thr Gly Pro Thr Gly Thr Asn Pro Pro
65                  70                  75                  80

Pro Pro Pro Ser Ala Asn Asn Pro Trp Thr Gly Phe Gln Ile Phe Leu
                85                  90                  95

Ser Pro Tyr Tyr Ala Asn Glu Val Ala Ala Ala Lys Gln Ile Thr
            100                 105                 110

Asp Pro Thr Leu Ser Ser Lys Ala Ala Ser Val Ala Asn Ile Pro Thr
        115                 120                 125

Phe Thr Trp Leu Asp Ser Val Ala Lys Ile Pro Asp Leu Gly Thr Tyr
130                 135                 140

Leu Ala Ser Ala Ser Ala Leu Gly Lys Ser Thr Gly Thr Lys Gln Leu
145                 150                 155                 160

Val Gln Ile Val Ile Tyr Asp Leu Pro Asp Arg Asp Cys Ala Ala Lys
                165                 170                 175

Ala Ser Asn Gly Glu Phe Ser Ile Ala Asn Asn Gly Gln Ala Asn Tyr
            180                 185                 190

Glu Asn Tyr Ile Asp Gln Ile Val Ala Gln Ile Gln Phe Pro Asp
        195                 200                 205

Val Arg Val Val Ala Val Ile Glu Pro Asp Ser Leu Ala Asn Leu Val
210                 215                 220

Thr Asn Leu Asn Val Gln Lys Cys Ala Asn Ala Lys Thr Thr Tyr Leu
225                 230                 235                 240

Ala Cys Val Asn Tyr Ala Leu Thr Asn Leu Ala Lys Val Gly Val Tyr
                245                 250                 255

Met Tyr Met Asp Ala Gly His Ala Gly Trp Leu Gly Trp Pro Ala Asn
            260                 265                 270

Leu Ser Pro Ala Ala Gln Leu Phe Thr Gln Val Trp Gln Asn Ala Gly
        275                 280                 285

Lys Ser Pro Phe Ile Lys Gly Leu Ala Thr Asn Val Ala Asn Tyr Asn
```

```
                    290                 295                 300
Ala Leu Gln Ala Ala Ser Pro Asp Pro Ile Thr Gln Gly Asn Pro Asn
305                 310                 315                 320

Tyr Asp Glu Ile His Tyr Ile Asn Ala Leu Ala Pro Leu Leu Gln Gln
                325                 330                 335

Ala Gly Trp Asp Ala Thr Phe Ile Val Asp Gln Gly Arg Ser Gly Val
            340                 345                 350

Gln Asn Ile Arg Gln Gln Trp Gly Asp Trp Cys Asn Ile Lys Gly Ala
        355                 360                 365

Gly Phe Gly Thr Arg Pro Thr Thr Asn Thr Gly Ser Gln Phe Ile Asp
    370                 375                 380

Ser Ile Val Trp Val Lys Pro Gly Gly Glu Cys Asp Gly Thr Ser Asn
385                 390                 395                 400

Ser Ser Ser Pro Arg Tyr Asp Ser Thr Cys Ser Leu Pro Asp Ala Ala
                405                 410                 415

Gln Pro Ala Pro Glu Ala Gly Thr Trp Phe Gln Ala Tyr Phe Gln Thr
            420                 425                 430

Leu Val Ser Ala Ala Asn Pro Pro Leu
            435                 440

<210> SEQ ID NO 3
<211> LENGTH: 1326
<212> TYPE: DNA
<213> ORGANISM: Artificial
<220> FEATURE:
<223> OTHER INFORMATION: Synthetic Construct - mutant of Phanerochaete
      chrysosporium
<220> FEATURE:
<221> NAME/KEY: CDS
<222> LOCATION: (1)..(1326)

<400> SEQUENCE: 3 atg cag gca tcg gag tgg gga cag tgc ggt ggc att ggt tgg act ggc      48
Met Gln Ala Ser Glu Trp Gly Gln Cys Gly Gly Ile Gly Trp Thr Gly
1               5                   10                  15 ccg acc act tgc gtc ccc ggt act acc tgc acg gtt ctc aat cca tac      96
Pro Thr Thr Cys Val Pro Gly Thr Thr Cys Thr Val Leu Asn Pro Tyr
            20                  25                  30 tac tcg cag tgc ttg cct gga tct gcg gtc acg acc acc tcc gtt atc     144
Tyr Ser Gln Cys Leu Pro Gly Ser Ala Val Thr Thr Thr Ser Val Ile
        35                  40                  45 acc agc cac tcg tcg tct gta tcc agc gta tcc tcg cat tcg ggc tct     192
Thr Ser His Ser Ser Ser Val Ser Ser Val Ser Ser His Ser Gly Ser
    50                  55                  60 tcc act tcg act tct tct ccc acg gga cct act ggc acc aac cct cct     240
Ser Thr Ser Thr Ser Ser Pro Thr Gly Pro Thr Gly Thr Asn Pro Pro
65                  70                  75                  80 cct cct ccg tcg gct aac aac ccc tgg act ggc ttc cag atc ttc ctc     288
Pro Pro Pro Ser Ala Asn Asn Pro Trp Thr Gly Phe Gln Ile Phe Leu
                85                  90                  95 agc cct tac tac gcg aac gag gtc gcc gct gct gct aag cag atc acg     336
Ser Pro Tyr Tyr Ala Asn Glu Val Ala Ala Ala Ala Lys Gln Ile Thr
            100                 105                 110 gat ccg act ctg tcc tct aag gct gcc agc gtt gca aac atc ccc act     384
Asp Pro Thr Leu Ser Ser Lys Ala Ala Ser Val Ala Asn Ile Pro Thr
        115                 120                 125 ttc acg tgg ctg gac tct gtc gcg aag atc cct gat ctc ggc acc tac     432
Phe Thr Trp Leu Asp Ser Val Ala Lys Ile Pro Asp Leu Gly Thr Tyr
    130                 135                 140 ctt gcc tct gct tct gca ctg ggc aag agc act ggc acc aag caa ctc     480
```

```
Leu Ala Ser Ala Ser Ala Leu Gly Lys Ser Thr Gly Thr Lys Gln Leu
145                 150                 155                 160 gtg caa att gtc atc tac gac ctg ccc gac cgt gac tgc gct gcc aag      528
Val Gln Ile Val Ile Tyr Asp Leu Pro Asp Arg Asp Cys Ala Ala Lys
                165                 170                 175 gcc tcc aac gga gag ttc agc att gcc aac aac gga caa gcc aac tac      576
Ala Ser Asn Gly Glu Phe Ser Ile Ala Asn Asn Gly Gln Ala Asn Tyr
            180                 185                 190 gag aac tac atc gac cag att gtt gct cag att caa cag ttc cct gat      624
Glu Asn Tyr Ile Asp Gln Ile Val Ala Gln Ile Gln Gln Phe Pro Asp
        195                 200                 205 gtc cgc gtc gtt gct gtg atc gag ccc gac tca ctc gcg aac ctg gtc      672
Val Arg Val Val Ala Val Ile Glu Pro Asp Ser Leu Ala Asn Leu Val
210                 215                 220 acc aac ctg aac gtc cag aag tgc gcc aac gcc aag acg acc tac ctt      720
Thr Asn Leu Asn Val Gln Lys Cys Ala Asn Ala Lys Thr Thr Tyr Leu
225                 230                 235                 240 gcc tgc gtg aac tac gcg ctc acc aac ctt gcc aag gtt ggc gtg tac      768
Ala Cys Val Asn Tyr Ala Leu Thr Asn Leu Ala Lys Val Gly Val Tyr
                245                 250                 255 atg tac atg gat gct ggc cac gcc ggc tgg ctc ggc tgg ccc gcg aac      816
Met Tyr Met Asp Ala Gly His Ala Gly Trp Leu Gly Trp Pro Ala Asn
            260                 265                 270 ctg tcg ccc gcc gcc cag ctc ttc acc cag gtc tgg cag aac gcc ggc      864
Leu Ser Pro Ala Ala Gln Leu Phe Thr Gln Val Trp Gln Asn Ala Gly
        275                 280                 285 aag tct cca ttc atc aag ggt ctc gcg acc aac gtc gcg aac tac aac      912
Lys Ser Pro Phe Ile Lys Gly Leu Ala Thr Asn Val Ala Asn Tyr Asn
290                 295                 300 gcc ctc cag gcc gcg tca ccc gac ccc atc acg cag ggc aac ccc aac      960
Ala Leu Gln Ala Ala Ser Pro Asp Pro Ile Thr Gln Gly Asn Pro Asn
305                 310                 315                 320 tat gac gaa atc cac tac atc aac gca ctc gcg ccc ttg ctc cag cag     1008
Tyr Asp Glu Ile His Tyr Ile Asn Ala Leu Ala Pro Leu Leu Gln Gln
                325                 330                 335 gcg ggc tgg gac gcg acc ttc atc gtc gac cag ggc cgc tcc ggt gta     1056
Ala Gly Trp Asp Ala Thr Phe Ile Val Asp Gln Gly Arg Ser Gly Val
            340                 345                 350 caa aac atc cgc caa cag tgg ggc gac tgg tgc aac atc aag ggc gcc     1104
Gln Asn Ile Arg Gln Gln Trp Gly Asp Trp Cys Asn Ile Lys Gly Ala
        355                 360                 365 ggc ttc ggt acc cgc ccg acg acg aac act ggc tcg cag ttc atc gac     1152
Gly Phe Gly Thr Arg Pro Thr Thr Asn Thr Gly Ser Gln Phe Ile Asp
370                 375                 380 tcc atc gtc tgg gtc aag ccc gga ggc gag tgc gac ggt acc tcc aac     1200
Ser Ile Val Trp Val Lys Pro Gly Gly Glu Cys Asp Gly Thr Ser Asn
385                 390                 395                 400 agc tcc tcg ccc cgc tac gac tcg act tgc tct ctg ccg gac gct gca     1248
Ser Ser Ser Pro Arg Tyr Asp Ser Thr Cys Ser Leu Pro Asp Ala Ala
                405                 410                 415 cag ccc gct cct gag gcc ggt acc tgg ttc cag gcg tac ttc cag acc     1296
Gln Pro Ala Pro Glu Ala Gly Thr Trp Phe Gln Ala Tyr Phe Gln Thr
            420                 425                 430 ctg gtt tct gct gcc aac ccg ccg ctg taa                             1326
Leu Val Ser Ala Ala Asn Pro Pro Leu
        435                 440
```

<210> SEQ ID NO 4
<211> LENGTH: 441
<212> TYPE: PRT
<213> ORGANISM: Artificial

-continued

```
<220> FEATURE:
<223> OTHER INFORMATION: Synthetic Construct

<400> SEQUENCE: 4

Met Gln Ala Ser Glu Trp Gly Gln Cys Gly Gly Ile Gly Trp Thr Gly
1               5                   10                  15

Pro Thr Thr Cys Val Pro Gly Thr Thr Cys Thr Val Leu Asn Pro Tyr
            20                  25                  30

Tyr Ser Gln Cys Leu Pro Gly Ser Ala Val Thr Thr Ser Val Ile
        35                  40                  45

Thr Ser His Ser Ser Ser Val Ser Ser Val Ser Ser His Ser Gly Ser
    50                  55                  60

Ser Thr Ser Thr Ser Ser Pro Thr Gly Pro Thr Gly Thr Asn Pro Pro
65                  70                  75                  80

Pro Pro Pro Ser Ala Asn Asn Pro Trp Thr Gly Phe Gln Ile Phe Leu
                85                  90                  95

Ser Pro Tyr Tyr Ala Asn Glu Val Ala Ala Ala Lys Gln Ile Thr
            100                 105                 110

Asp Pro Thr Leu Ser Ser Lys Ala Ala Ser Val Ala Asn Ile Pro Thr
            115                 120                 125

Phe Thr Trp Leu Asp Ser Val Ala Lys Ile Pro Asp Leu Gly Thr Tyr
            130                 135                 140

Leu Ala Ser Ala Ser Leu Gly Lys Ser Thr Gly Thr Lys Gln Leu
145                 150                 155                 160

Val Gln Ile Val Ile Tyr Asp Leu Pro Asp Arg Asp Cys Ala Ala Lys
                165                 170                 175

Ala Ser Asn Gly Glu Phe Ser Ile Ala Asn Asn Gly Gln Ala Asn Tyr
            180                 185                 190

Glu Asn Tyr Ile Asp Gln Ile Val Ala Gln Ile Gln Gln Phe Pro Asp
        195                 200                 205

Val Arg Val Val Ala Val Ile Glu Pro Asp Ser Leu Ala Asn Leu Val
            210                 215                 220

Thr Asn Leu Asn Val Gln Lys Cys Ala Asn Ala Lys Thr Thr Tyr Leu
225                 230                 235                 240

Ala Cys Val Asn Tyr Ala Leu Thr Asn Leu Ala Lys Val Gly Val Tyr
                245                 250                 255

Met Tyr Met Asp Ala Gly His Ala Gly Trp Leu Gly Trp Pro Ala Asn
            260                 265                 270

Leu Ser Pro Ala Ala Gln Leu Phe Thr Gln Val Trp Gln Asn Ala Gly
        275                 280                 285

Lys Ser Pro Phe Ile Lys Gly Leu Ala Thr Asn Val Ala Asn Tyr Asn
290                 295                 300

Ala Leu Gln Ala Ala Ser Pro Asp Pro Ile Thr Gln Gly Asn Pro Asn
305                 310                 315                 320

Tyr Asp Glu Ile His Tyr Ile Asn Ala Leu Ala Pro Leu Leu Gln Gln
                325                 330                 335

Ala Gly Trp Asp Ala Thr Phe Ile Val Asp Gln Gly Arg Ser Gly Val
            340                 345                 350

Gln Asn Ile Arg Gln Gln Trp Gly Asp Trp Cys Asn Ile Lys Gly Ala
        355                 360                 365

Gly Phe Gly Thr Arg Pro Thr Thr Asn Thr Gly Ser Gln Phe Ile Asp
    370                 375                 380

Ser Ile Val Trp Val Lys Pro Gly Gly Glu Cys Asp Gly Thr Ser Asn
385                 390                 395                 400
```

```
Ser Ser Ser Pro Arg Tyr Asp Ser Thr Cys Ser Leu Pro Asp Ala Ala
            405                 410                 415

Gln Pro Ala Pro Glu Ala Gly Thr Trp Phe Gln Ala Tyr Phe Gln Thr
            420                 425                 430

Leu Val Ser Ala Ala Asn Pro Pro Leu
        435                 440
```